United States Patent
Chevalier et al.

(10) Patent No.: US 6,641,816 B1
(45) Date of Patent: Nov. 4, 2003

(54) USE OF POXVIRUSES AS ENHANCER OF SPECIFIC IMMUNITY

(75) Inventors: Michel Chevalier, Beaurepaire (FR); Bernard Meignier, Thurins (FR); Catherine Moste, Charbonnieres-les-Bains (FR); Suryaprakash Sambhara, Markham (CA)

(73) Assignee: Aventis Pasteur S.A., Lyons Cedex (FR)

( * ) Notice: Subject to any disclaimer, the term of this patent is extended or adjusted under 35 U.S.C. 154(b) by 0 days.

(21) Appl. No.: 09/720,466

(22) PCT Filed: Jun. 28, 1999

(86) PCT No.: PCT/EP99/04913
§ 371 (c)(1), (2), (4) Date: Mar. 9, 2001

(87) PCT Pub. No.: WO00/00216
PCT Pub. Date: Jan. 6, 2000

(30) Foreign Application Priority Data

Jun. 26, 1998 (EP) ............................................. 98420110
Jun. 26, 1998 (EP) ............................................. 98420111

(51) Int. Cl.[7] ..................... A61K 39/12; A61K 39/275; A61K 39/285; C12N 7/01; C12N 7/04
(52) U.S. Cl. ................. 424/191.1; 424/93.2; 424/205.1; 424/206.1; 424/207.1; 424/232.1; 435/236; 435/320.1
(58) Field of Search .............................. 424/93.2, 205.1, 424/206.1, 207.1, 232.1, 191.1; 435/236, 320.1

(56) References Cited

U.S. PATENT DOCUMENTS 5,863,542 A * 1/1999 Paoletti et al. ............ 424/199.1
6,180,398 B1 * 1/2001 Klein et al. ............... 435/320.1

FOREIGN PATENT DOCUMENTS

| WO | WO9308836 | 5/1993 |
| WO | WO9522978 | 8/1995 |
| WO | WO9527507 | 10/1995 |
| WO | WO9640268 | 12/1995 |

OTHER PUBLICATIONS

Clement–Mann et al. J. Inf. Dis. 1998, vol. 177, pp. 1230–1246.*
Kent et al. J. Immunol. 1997, vol. 158, pp. 807–815, abstract.*
Franchini et al. Aids Reasearch and Human Retrovirus, 1995, Vol 11, pp. 307–313.*
Muthian et al. Aids Research and Human Retroviruses, 1994, vol. 10, pp. 839–851.*
Cohen, Science 1999, vol. 235, pp. 656–657.*
Pialoux et al. Aids Research and Human Retrovirus, 1995, Vol 11, pp. 373–381.*
Hu et al. Science 1992, Vol 255, pp. 456–459.*
Hammond et al. J. Exp. Med. 1992, vol. 176, pp. 1531–1542.*
Andersson et al. J. Inf. Dis. 1996, vol. 174, pp. 977–985.*
Myagkih Aids Research and Human Retroviruses 1996, vol. 11, pp. 985–992.*
A. Mayr., et al. "Bekämpfung des ecthyma contagiosum (pustulardermatitis) der schafe mit einem neuen parenteral–zellkultur–lebendimpfstoff". *Zentralblatt für Veterinärmedizin, Reihe B*, vol. 28, No. 7, 1981. pp. 535–552.
A. Mayr., et al. "Vergleichende untersuchungen über die immunstimulierende (paramunisierende) wirksamkeit von BCG, levamisol, corynebacterium parum und präparaten aus pockenviren in verschiedenen 'in vivo' und 'in vitro' testen". *Zentralblatt für Veterinärmedizin, Reihe B*, vol. 33, 1986. pp. 321–339.
M. L. Clements–Mann et al. Immune Responses to Human Immunodeficiency Virus (HIV) Type 1 Induced by Canarypox Expressing HIV–1mn gp120, HIV–1sf2 Recombinant gp120, or both Vaccines in Seronegative Adults. *Journal of Infectious Diseases*, vol. 177, No. 5, May 1998. pp. 1230–1246.

* cited by examiner

Primary Examiner—James Housel
Assistant Examiner—Bao Qun Li
(74) Attorney, Agent, or Firm—McDonnell Boehnen Hulbert & Berghoff

(57) ABSTRACT

The invention relates to a method for enhancing the specific immune response against an immunogenic compound which comprises administering the immunogenic compound together with a poxvirus recombinant and a vaccinal antigen, which is not a poxvirus. The immunological material may be any biological material useful as a vaccine e.g., a polypeptide characteristic of a pathogenic microorganism or associated with a tumoral disorder, a DNA plasmid encoding a peptide or a polypeptide characteristic of a pathogenic microorganism or a tumor-associated antigen, or an hapten coupled to a carrier molecule. The poxvirus may be a live, attenuated or inactivated virus or a recombinant virus. Recombinant virus may encode a heterologous polypeptide such as chemokines, cytokines or co-immunostimulatory molecules or an homologous polypeptide, which is immunologically cross reactive with the immunogenic polypeptide or peptide.

28 Claims, 17 Drawing Sheets

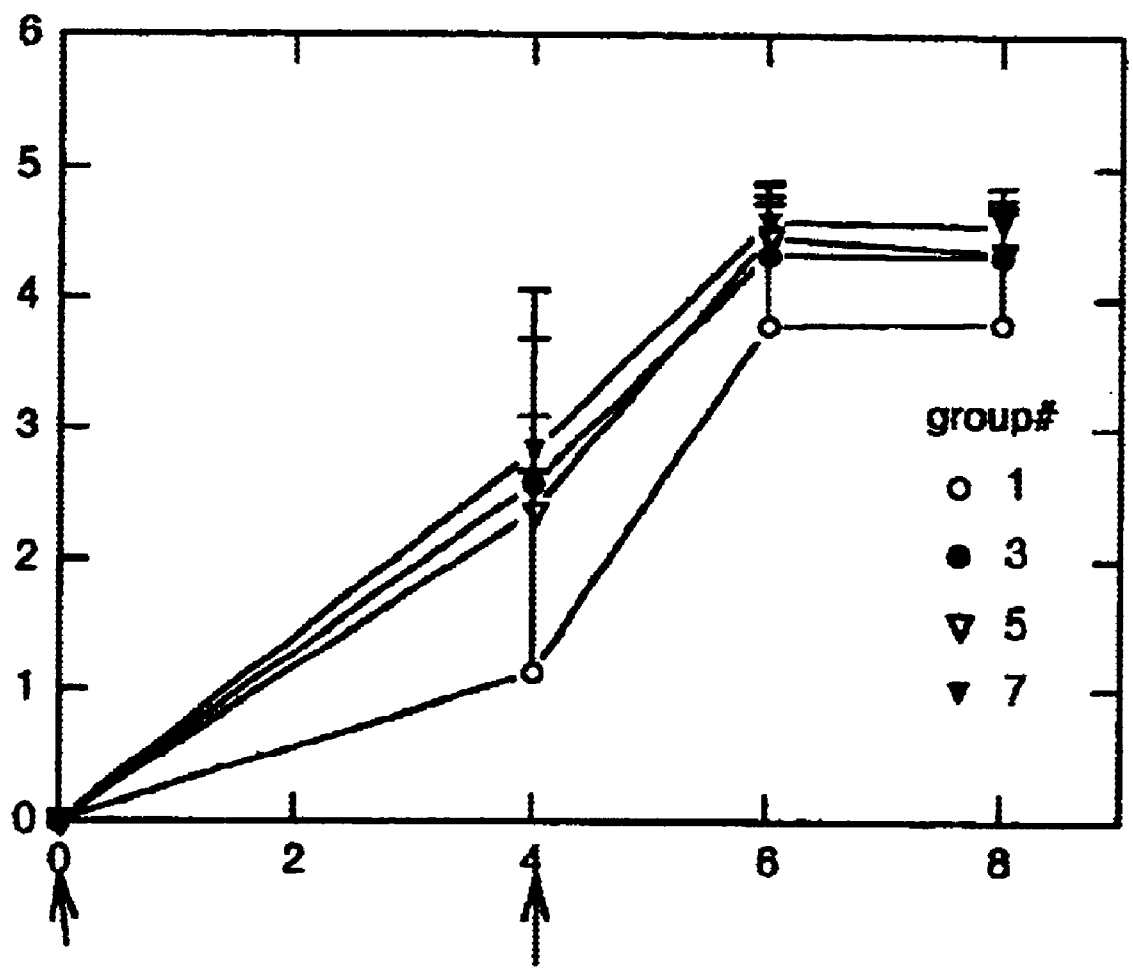

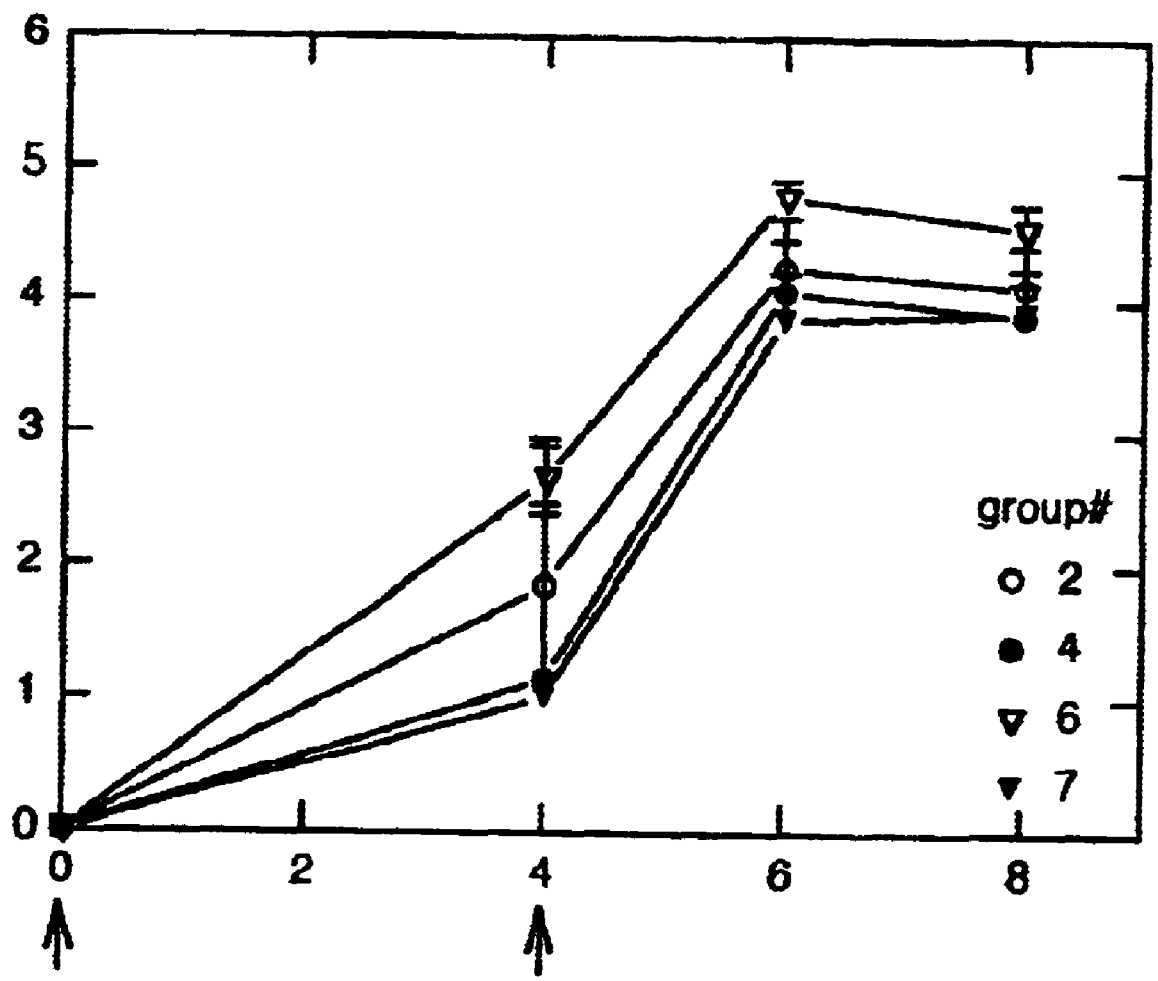

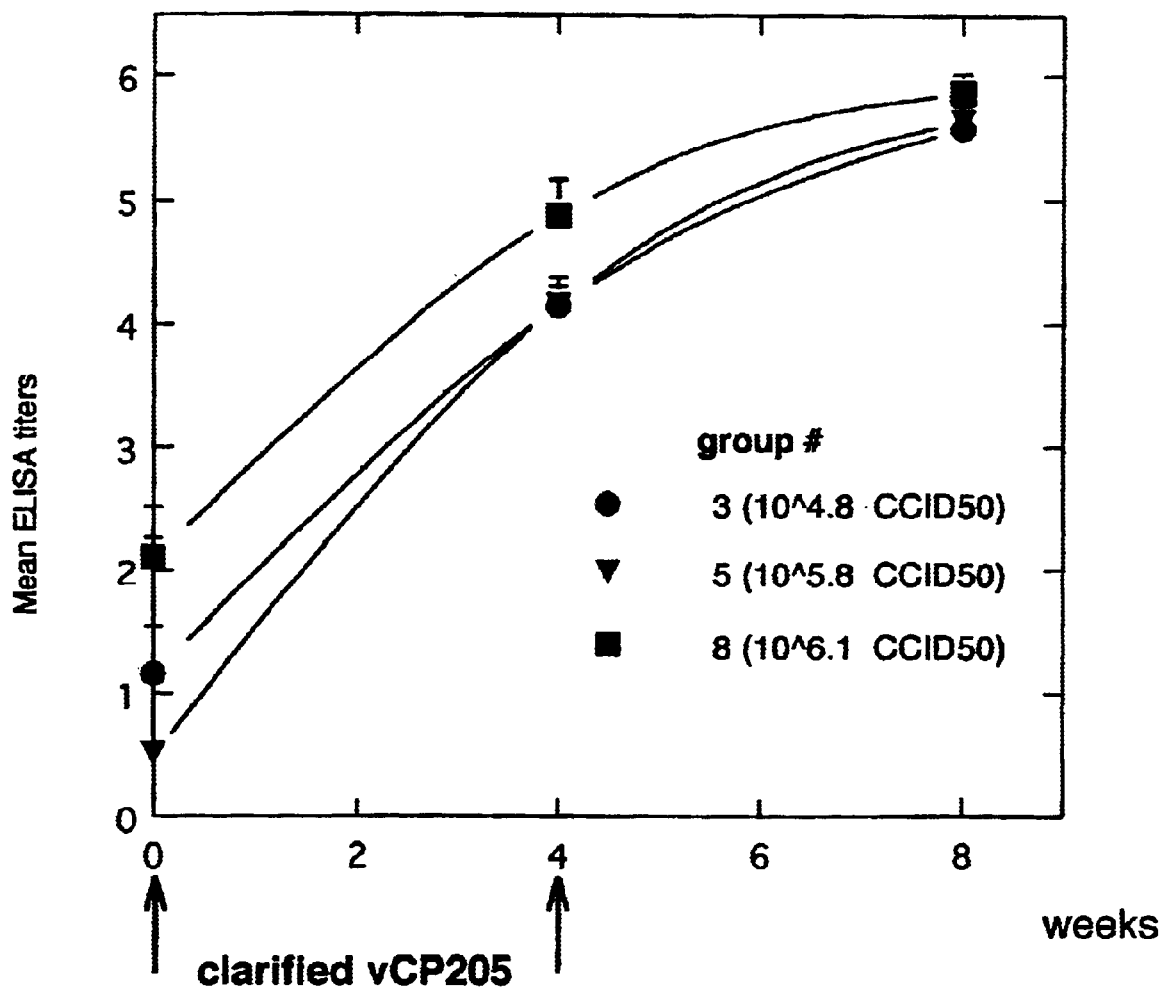

clarified vCP205 and/or gp160MN/LAI

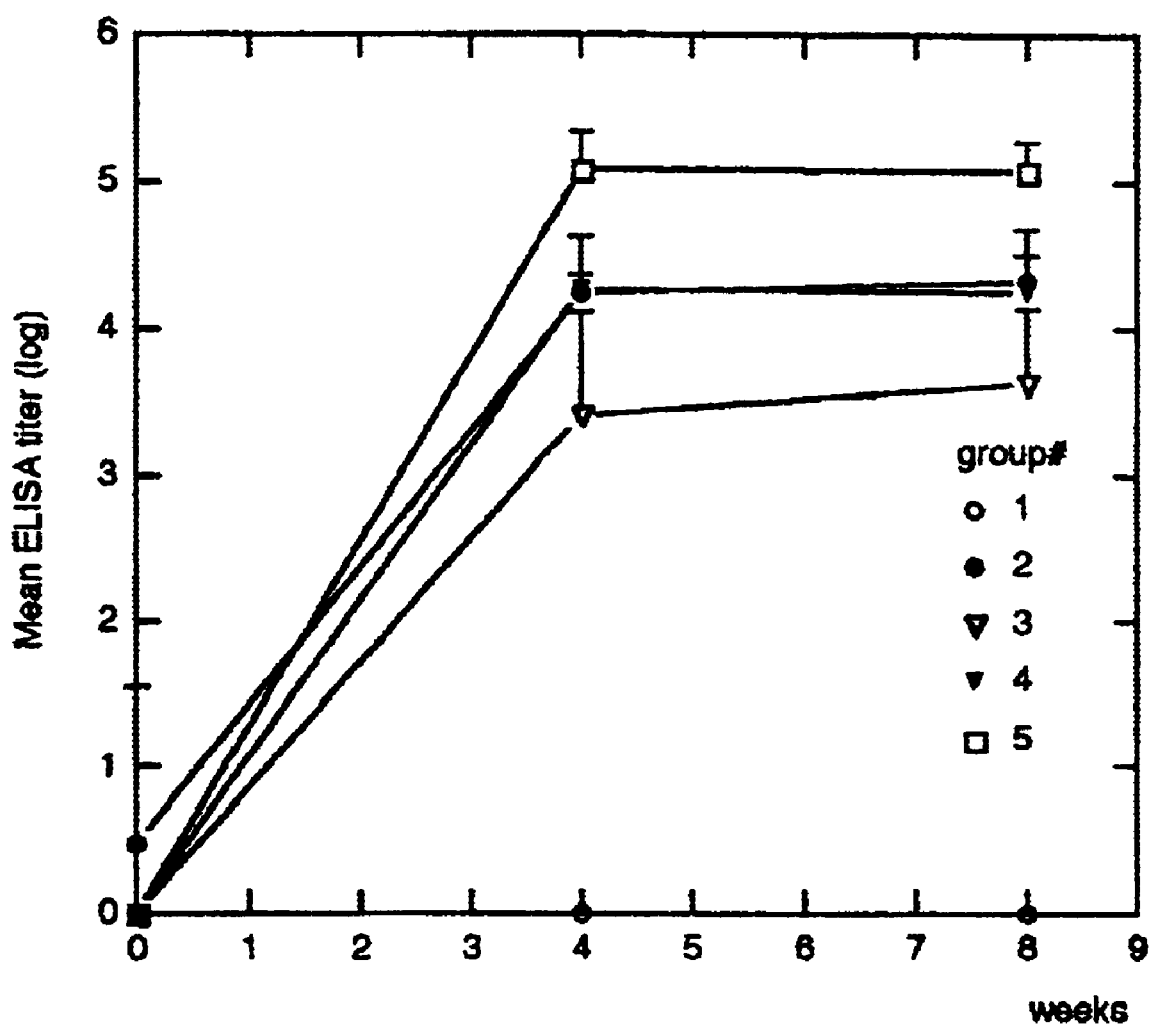

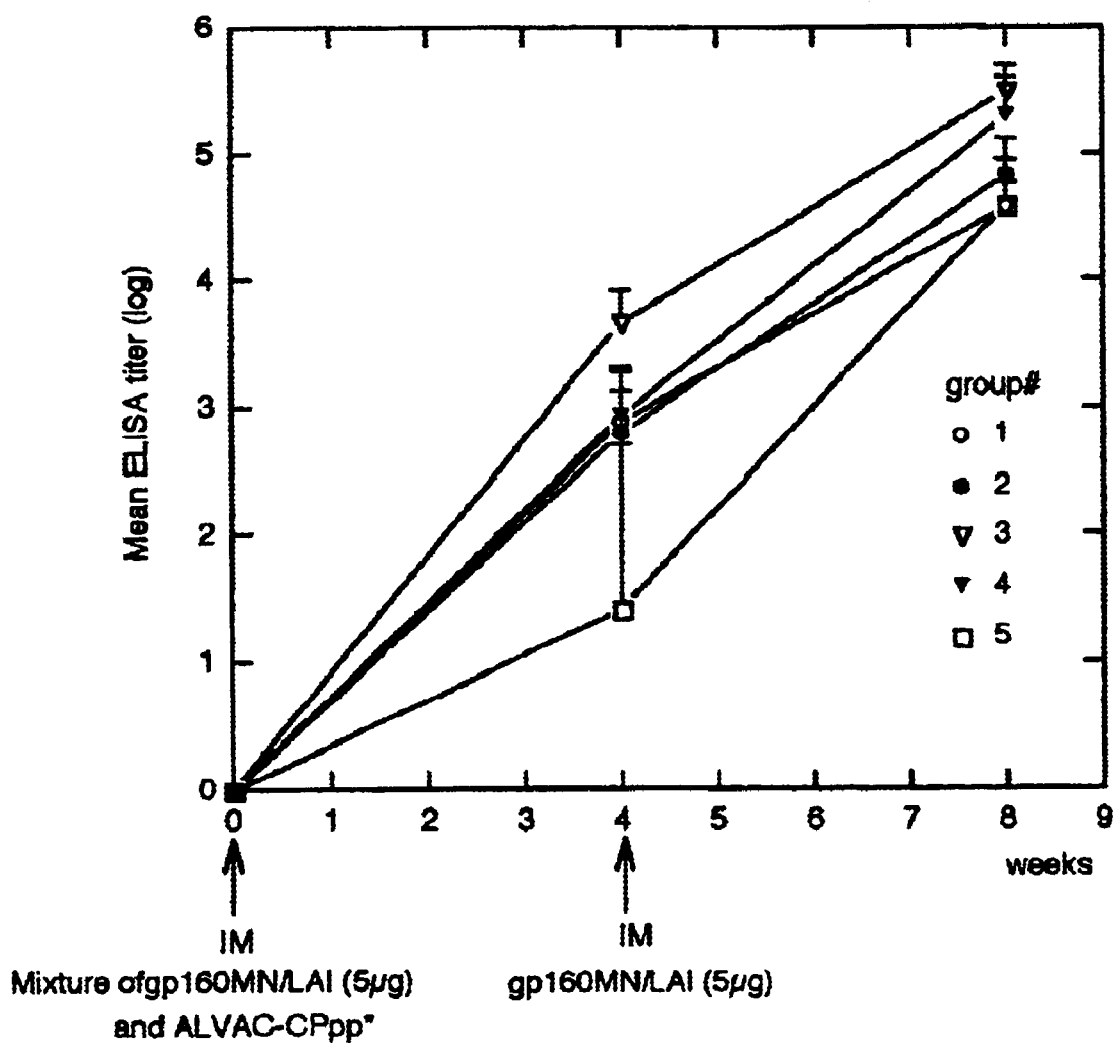

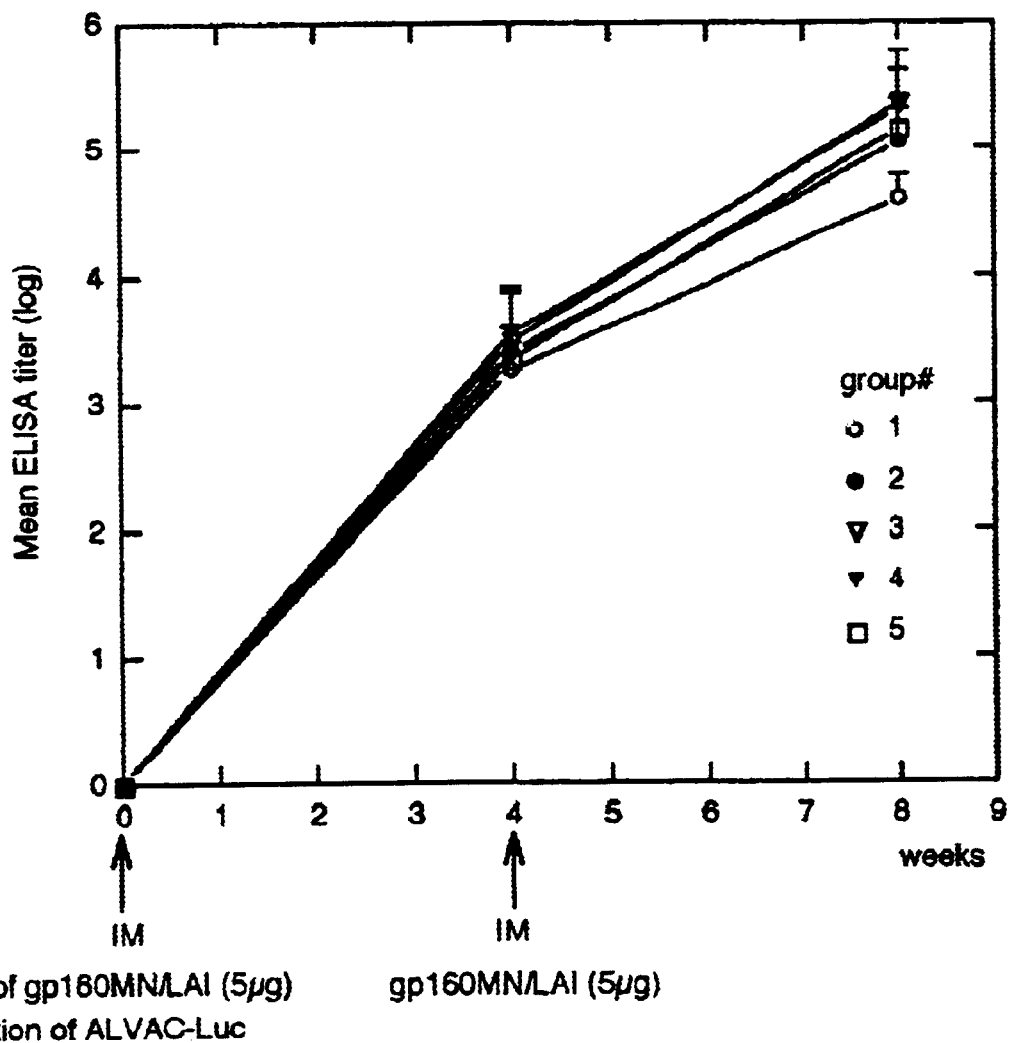

USE OF POXVIRUSES AS ENHANCER OF SPECIFIC IMMUNITY

Figure 1B:
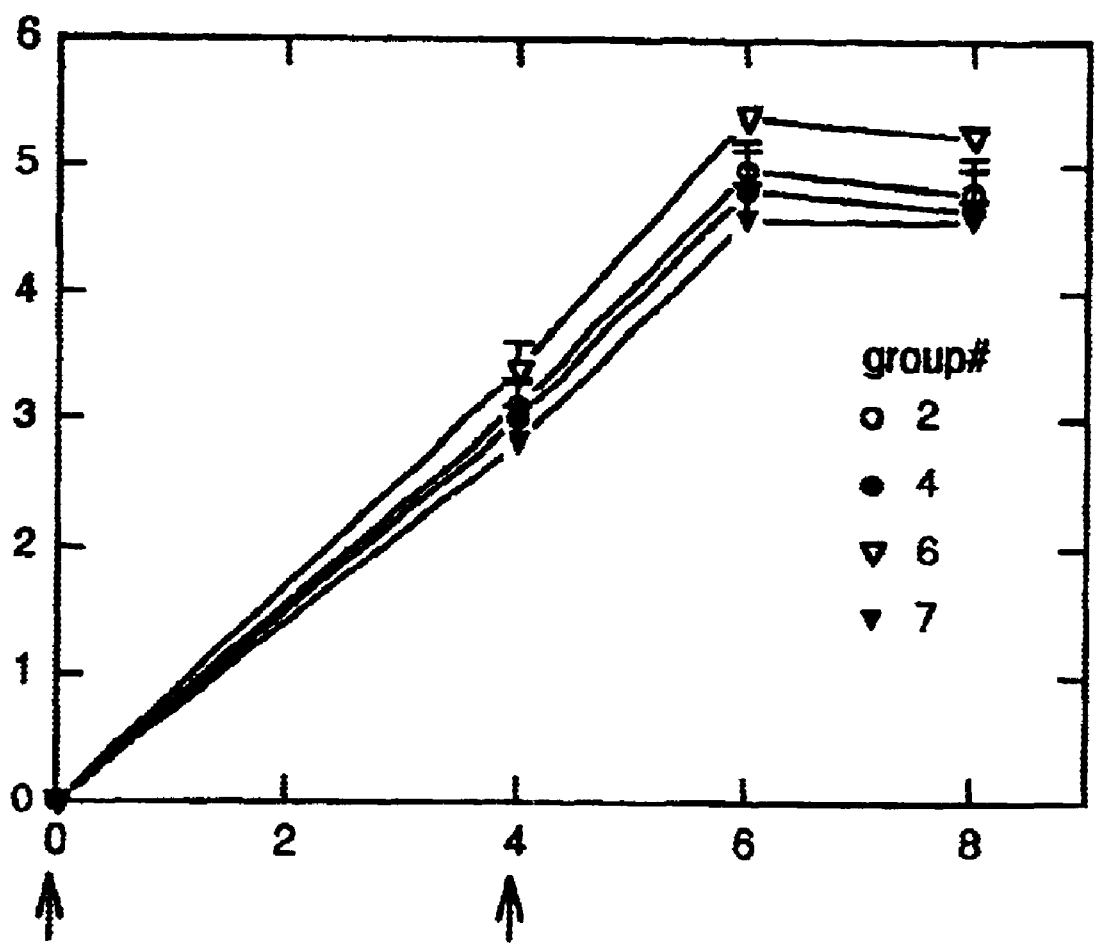

The present invention relates to a method for enhancing the specific immune response against an immunogenic compound, which comprises administering the immunogenic compound together with a poxvirus, recombinant or not.

Smallpox, a human infectious disease due to a vaccinia virus, was declared eradicated from the globe in 1980. This unique success was made possible by the availability of an effective virus-attenuated vaccine. Concurrent with the smallpox eradication and the cessation of vaccination, a new use for the vaccinia virus was proposed (Panicali & Paoletti, PNAS (1982) 79:4927). Utilizing molecular cloning techniques, it became possible to express genes from foreign pathogens in vaccinia virus providing new approaches to vaccination.

Since then, the original technology has been applied to the whole poxvirus family, including not only the vaccinia virus but also avipoxviruses such as fowlpox and canarypox. In order to address the issue of safety, a strategy was developed to genetically engineer a highly attenuated vaccinia virus such as the Copenhagen strain that would still retain the ability to induce vigorous immunological response against extrinsic antigens. A number of poxvirus constructions have been tested in clinical trials. As a matter of example, they include recombinant vaccinia and canarypoxviruses expressing Human Immunodeficiency Virus (HIV) or *Plasmodium falciparum* antigens. Further, it has already been proposed to combine, in an immunization protocol, a prime-administration using a recombinant poxvirus vector and booster-administrations of the purified polypeptide as encoded by the recombinant vector (See e.g., Excler & Plotkin, AIDS (1997) 11 (suppl. A): S127). Such immunization protocols are commonly referred as prime-boost protocols and are very advantageous in a number of cases, in particular for AIDS treatment or prevention.

Prime-boost protocols are however unpractical both for physicians, manufacturers and sellers, in that they require two different pharmaceutical products that have to be each identified and licensed for their specific use (priming or boost).

It has now been found that poxvirus particles may be useful as enhancer of specific immunity. Indeed, it has been observed that the immune response against a vaccinal antigen, such as an HIV or an influenza virus protein, is enhanced, when it is mixed with a poxvirus, recombinant or not. Additionally, It has also been found that an immunization protocol exclusively using a composition comprising a polypeptide and a poxvirus encoding this polypeptide, may be just as good as a prime-boost protocol. It has also surprisingly been found that the observed immunization effect is not a mere additional effect, but results from a synergism effect between the two components.

Therefore, the invention provides for:

(i) The use of a poxvirus for the manufacture of a pharmaceutical composition comprising an immunogenic compound for inducing an immune response in a vertebrate, wherein the poxvirus is able to enhance a specific immune response to the immunogenic compound.

(ii) The use of a mixture comprising (a) an immunogenic compound which comprises at least one antigenic determinant characteristic of a pathogenic microorganism or is cross-reactive with a tumor-associated antigen (TAA) and (b) a poxvirus; in the manufacture of a medicament to be administered to a vertebrate for treating or preventing an infection induced by the pathogenic microorganism or a tumoral disorder characterized by the malignant expression of the TAA; whereby said poxvirus enhances the specific immune response of the vertebrate against said immunogenic compound.

(iii) A pharmaceutical composition comprising (a) an immunogenic compound and (b) a poxvirus encoding an heterologous polypeptide which is selected from the group consisting of adhesion molecules, co-immunostimulatory molecules, apoptotic factors, cytokines, chemokines and growth hormones.

(iv) A pharmaceutical composition comprising (a) an immunogenic compound which is a first polypeptide and (b) a poxvirus encoding an heterologous polypeptide, which has an amino acid sequence identical to the amino acid sequence of the first polypeptide.

(v) A pharmaceutical composition comprising (a) an immunogenic compound which is a DNA plasmid encoding a first polypeptide and (b) a poxvirus encoding a second heterologous polypeptide, which has an amino acid sequence identical to the amino acid sequence of the first polypeptide.

(vi) A method for enhancing the specific immune response of a vertebrate to an immunogenic compound, which comprises administering to the vertebrate the immunogenic compound together with a poxvirus, whereby the poxvirus enhances the specific immune response to the immunogenic compound.

(vii) A method for treating or preventing in a vertebrate, a disorder either induced by a pathogenic microorganism or characterized by the malignant expression of a T.A.A, which comprises administering to the vertebrate, (a) an immunogenic compound which comprises at least one antigen determinant characteristic of the pathogenic microorganism or a tumor-associated antigen together with (b) a poxvirus; whereby a specific immune response to the immunogenic compound is induced in the vertebrate and whereby the poxvirus enhances the specific immune response.

(viii) A method for enhancing the specific "in vitro" immunostimulation of cells from an immune system against a specific immunogenic compound, which comprises (a) recovering cells from a vertebrate, (b) "in vitro" incubating the cells with the immunogenic compound together with a poxvirus, whereby the cells are immunostimulated against the immunogenic compound and whereby the poxvirus enhances the immunostimulation and (c) administering the immunostimulated cells obtained from step (b) to a vertebrate.

In a general manner, there exist two types of immunity: the innate immunity and the acquired immunity. The former which is phylogenetically older brings into play soluble molecules, i.a. complement factors and cells, such as NK cells or macrophages, which are innately programmed to detect noxious substances produced by pathogenic microorganisms and to provide for rapid but often incomplete antimicrobial host defense. The innate immune system intervenes as the first line of defense when an infectious agent attacks an individual. On the other hand, the innate immune system can not be educated by the antigens expressed by the pathogenic microorganisms or tumor cells during the life of an individual and in this respect; the innate immunity is confounded with the natural immunity. By contrast, the acquired immune system brings into play antigen-specific B and T lymphocyte clones the affinity of which increases by the time consecutively to repeated contacts with the specific antigen. Moreover, some of them behave as memory lymphocytes, since they have a long lasting life and are able to proliferate and expand rapidly consecutively to a further contact with a specific antigen, so that these memory lymphocytes contribute to the long term protection of an individual to infectious microorganisms. An essential goal of vaccination is to provide for these memory lymphocytes.

Accordingly, by "specific immune response" is meant a specific humoral and/or a specific cellular immune response against the immunogenic compound of the pharmaceutical composition. In the present invention, the specific humoral immune response includes both systemic and mucosal antibody responses since, to feature the humoral response, one may refer to all types of specific antibodies, i.e. IgM, all subclasses of IgG and IgA, that may be elicited by the pharmaceutical composition. The specific lymphoproliferative response and the specific cytotoxic T lymphocyte (CTL) response preferentially are the main parameters of the specific cellular immune response.

For use in the present invention, the immunogenic compound may be a chemical or a biological material that is able to induce a humoral or cellular immune response in a vertebrate. A biological material may be e.g., an attenuated, inactivated or killed virus (to the exception of a poxvirus); a bacterial strain; a pseudovirion; a bacterial extract; a capsular polysaccharides; a peptide or a polypeptide found tumor-associated, cross-reactive with a TAA or characteristic of a pathogenic agent; or a DNA plasmid encoding a peptide or a polypeptide as described above. As an example of chemical material, a hapten coupled to a carrier protein is cited.

By "hapten" is meant a molecule, generally of low molecular weight, which is unable to trigger an antibody response by itself, but capable, after coupling with a carrier, to induce a specific antibody response which interacts specifically with the hapten molecule. For use in the present invention, such an hapten may be a peptide which amino acid sequence is at least 5 to 6 amino acid long (minimal size of an epitope) but of low molecular weight, a chemical molecule (such as dinitrophenol), or a drug. In a particular embodiment of the present invention, a mixture according to the invention may be intended to treat drug addiction and to this end, may comprise a poxvirus, mixed with a drug, such as cocaine, coupled to a carrier molecule to induce an antibody response against the drug, in order to hamper both its fixation on the target cells, tissues or organs and the triggering of its narcotic effects. Methods of coupling a hapten to a carrier molecule are of common use for a man skilled in the art.

By "polypeptide" or "protein" is meant any chain of amino acids, regardless of the length or post-translational modification (e.g., glycosylation or phosphorylation). Both terms are used interchangeably in the present application.

Advantageously, immunogenic polypeptides may be polypeptides characteristic of a pathogenic microorganism i.e. a virus, bacteria or an eucaryotic parasite, or tumor-associated antigens (that are mammalian or avian antigens which are not normally expressed; their malignant expression is characteristic of a tumoral disorder) such as tyrosinase, the MAGE protein family, the CEA, the ras protein, mutated or not, the p53 protein, mutated or not, Muc1, CEA and pSA.

For use in the present invention, immunogenic polypeptides may have amino acid sequences corresponding to the complete or partial sequence of naturally occurring polypeptides. They may also have a sequence derived by amino acid deletion, addition or substitution from the naturally occurring sequences as far as they behave as immunologic equivalents i.e., they are able to induce an immune response against the pathogenic microorganisms from which they derive or against the tumor. In other terms, an immunogenic polypeptide is also meant to include any polypeptide that is immunologically cross-reactive with a naturally occurring polypeptide found in a pathogenic agent or tumor-associated.

By "immunologically cross-reactive polypeptides" is meant polypeptides that can be recognized by antibodies, e.g. polyclonal antibodies, raised against each of the polypeptides used separately, and advantageously in a substantially purified form.

As a matter of example, the polypeptide may be an HIV antigen such as the env, gag, pol or nef protein. An HIV antigen is also meant to include any polypeptide that is immunologically cross-reactive with a naturally occurring HIV protein. For example, an HIV env protein may be the gp160 env precursor, or the gp120 or gp41 sub-unit. The gp160 precursor may be a soluble, non-cleavable precursor obtained by mutation of the cleavage site and deletion of the transmembrane region as described in U.S. Pat. No. 5,672,689. The precursor may also be truncated so that the C-terminal part of the gp41 region is removed (intracytoplasmic domain). The precursor may also be a hybrid precursor, combining in a single molecule, env sequences from various HIV strains. An HIV gag antigen may be the complete p55 precursor, the p13, p18 or p25 that naturally derive from p55, or any immunogenic gag protein fragment. In fact, a large variety of polypeptides may be substituted for the naturally occurring HIV env, gag, pol or nef proteins, yet retaining their immunogenic properties.

As an additional example the polypeptide may be an influenza peptide or polypeptide which comprises the virus envelope components such as the haemagglutinin and the neuraminidase and the virus internal components such as the protein M, the non-structural proteins and the nucleoprotein. An influenza peptide or polypeptide is also meant to include any precursor form of the mature envelope or internal proteins that are immunologically cross reactive with them. Likewise, the polypeptide or peptide may be any kind of haemagglutin or neuraminidase of the influenza virus since there are numerous antigenic variants of these two proteins.

For use in the present invention, the polypeptide characteristic of a pathogenic agent that is physically present in the composition may be purified from the pathogenic agent itself or recombinantly produced. Advantageously tumor-associated antigens (TAAs) as well will be produced by recombinant means. Standard expression vectors, promoters, terminators, etc and recombinant methods are now of common use for a man skilled in the art and recombinant expression can be readily achieved once an appropriate DNA sequence corresponding to the polypeptide is available. In a particular embodiment, polypeptides may be recombinantly produced as fusion polypeptides (i.e., a polypeptide fused through its N- or C-terminal end to any other polypeptide (hereinafter referred to as a peptide tail), using appropriate expression vectors, such as the pMal-c2 or pMal-p2 systems of New England Biolabs in which the peptide tail is a maltose binding protein, or the His-Tag system available from Novagen.

An immunogenic compound, e.g., a polypeptide physically present in a composition of the invention is advantageously present in a substantially purified form, i.e., it is separated from the environment in which it naturally occurs and/or is free of the majority of the polypeptides that are present in the environment in which it was synthesized.

As mentioned above, the immunogenic compound may also be a DNA plasmid unable to replicate in eucaryotic cells, comprising a DNA sequence encoding a peptide or a polypeptide, this latter being defined as herein above, under the control of an appropriate promoter which allows the peptide or polypeptide to be expressed in eucaryotic cells after transfection by the recombinant plasmid. As a matter of example, the CMV (Cytomegalovirus) early promoter is broadly used for the expression of a heterologous peptide or polypeptide in human cells transfected with DNA plasmid encoding peptide or polypeptide.

In a particular embodiment of the present invention, a DNA plasmid advantageously encodes a peptide comprising one or several epitopes characteristic of a viral, bacterial, parasitic, or tumor-associated polypeptide. As a matter of example, it is well known that tumor-associated antigens, such as Her-2 neu, are often poor immunogens, because they are essentially "self" antigens. To overcome the lack of immunogenicity, it is commonly proposed to use as an immunogenic compound, instead of DNA encoding the whole polypeptide, a DNA encoding "subdominant" epitopes selected from the polypeptide. This strategy is also applicable to infectious microorganisms, such as HIV, Mycobacterium tuberculosis or Plasmodium falciparum for which the protective antigens are not yet defined. In a particular embodiment of the invention, aimed at the induction or the enhancement of a specific CTL response in a variety of Major Histocompatibility Complex (MHC) contexts, a pharmaceutical composition comprising a poxvirus mixed together with a DNA plasmid encoding customized peptides, may be useful. A customized peptide comprises or mimics an epitope selected throughout the whole amino acid sequence of an antigen of a pathogenic micro-organism or a tumor, as containing putative anchor motifs needed for binding to various MHC class I molecules (such as in humans, HLA-A1, HLA-A2, HLA-B7, . . . ). The customized peptides encoded by the plasmid may all together preferably trigger a specific CTL response in the main MHC contexts, of a given vertebrate.

For use in the present invention, the poxvirus may be any virus belonging to the poxviridae family. Accordingly, useful poxviruses include, capripoxvirus, suipoxvirus, molluscipoxvirus, yatapoxvirus, entomopoxvirus, orthopoxvirus and avipoxvirus; these two latter being preferred. A typical orthopoxvirus is a vaccinia virus. A suitable vaccinia virus may be e.g., the highly attenuated Copenhagen strain or the NYVAC vector that is derived from the Copenhagen strain by precise deletion of 18 open reading frames (ORFs) from the viral genome as described in Tartaglia et al, Virology (1992) 188:217. A typical avipoxvirus is a canarypoxvirus or a fowl poxvirus. A suitable canarypoxvirus may be e.g., the ALVAC vector obtained as described in Tartaglia et al (supra). A suitable fowlpox vector may be e.g., the TROVAC vector which is a plaque-cloned isolate derived from the FP-1 vaccine strain licensed for vaccination of 1 day old chicken (sold by Merial, Lyon, France) and described in Taylor et al, Vaccine (1988) 6: 497.

A poxvirus for use in the present invention may be a live, attenuated or inactivated virus. By "live virus" is meant a virus that is fully capable to reproduce its natural infectious cycle into sensitive cells, comprising virus entry, uncoating, gene expression, DNA replication, virus assembly, maturation and release. In a particular embodiment, a live virus may be attenuated. Attenuated virus may be obtained, e.g., by selection-of spontaneous mutants after repeated infectious cycles into sensitive cells, by selective pressure or deletion of non-essential genes using molecular biology tools. Nevertheless, whatever the process of attenuation, the viruses that are issued remain able to reproduce themselves into sensitive cells even if sometimes the spectrum of sensitive cells can decrease. As a matter of example, it may be useful to delete the vaccinia virus genome from K3L or E3L genes to render it more sensitive to the action of interferons and consequently to reduce its host restriction range (Beattie E and al., (1996) Virus Genes, 12, 89–94). As a matter of example a suitable live virus for use in humans may be a canarypoxvirus, since in human cells such a virus exhibits an abortive infectious cycle. Additionally a suitable attenuated virus for use in humans may be a NYVAC vector. By "inactivated virus" is meant a virus that is no more capable to reproduce its entire infectious cycle into sensitive cells as a result of either a mechanical, chemical or physical treatment. As may be easily understood, inactivation is particularly advantageous when a non-recombinant poxvirus is used.

For use in the present invention, a poxvirus may be recombinant or not. A non-recombinant poxvirus does not encode any heterologous polypeptide. On the other hand, a recombinant virus is typically a virus in the genome of which is inserted one or several foreign genes (e.g. an heterologous coding sequence located in the genome under the control of a viral promoter allowing at least a transient expression in the virus-infected cells).

A useful recombinant poxvirus encodes a heterologous peptide or polypeptide that may be of any kind. In one embodiment of the invention, the peptide or the polypeptide may be a cytokine, such as interleukin-2. (IL-2), interleukin-3 (IL-3) interleukin-12 (IL-12), interleukin-15 (IL-15), interleukin-18 (IL-18) and granulocyte macrophage-colony stimulating factor (GM CSF); a chemokine, such as RANTES (Regulated on Activation Normal T-cell Expressed and Secreted) and MCP1 (Monocyte Chemotactic protein 1); a co-immunostimulatory molecule, such as B7, CD40, CD40L and ICAMs (inter cellular adhesion molecules); an adhesion molecule; an apoptotic factor, such as p53 and TNF (tumor necrosis factor); or an hormone such as a growth hormone.

In another embodiment, the immunogenic compound for use in the present invention is a peptide or a polypeptide and the admixed poxvirus encodes a heterologous peptide or polypeptide that cross-reacts with the immunogenic compound. Accordingly, the invention also features the use of a poxvirus for the manufacture of a pharmaceutical composition comprising a first polypeptide; wherein the poxvirus encodes a second polypeptide which immunologically cross reacts with the first polypeptide. The encoded polypeptide may be the same as the one present in the composition. In other words, the encoded polypeptide has an amino acid sequence identical to that of the polypeptide present in the composition. Alternatively, the poxvirus may encode an immunogenic polypeptide that is similar to the polypeptide present in the composition, although slightly different at the amino acid sequence level. In a particular embodiment, the immunogenic polypeptide present as such in the composition originates from a particular pathogenic strain and the poxvirus vector accompanying the polypeptide encodes an allelic variant thereof i.e., the same polypeptide but from another strain. As a result, the polypeptide physically present and the encoded polypeptide may have amino acid sequences slightly different, being at least 70, 80, 90% or more identical. A composition comprising the HIV MN gp120 together with a poxvirus encoding HIV LAI gp120 is cited as a matter of example. In another embodiment, the sequences of both the polypeptide physically present and the encoded polypeptide may derive from each other by addition, deletion or substitution of one or several amino acids, provided that these polypeptides are immunologically cross-reactive. As a matter of example, it is cited a composition comprising:

(i) HIV gp160 and a poxvirus encoding HIV gp120;

(ii) HIV gp160 in a soluble and non-cleavable form and a poxvirus encoding wild-type gp160;

(iii) HIV gag p55 and a poxvirus encoding gag p18; or (iv) HIV gp120 and a poxvirus encoding HIV gp120-p18 hybrid protein; or (v) HIV gp120, HIV p18 and a poxvirus encoding HIV gp120-p18 hybrid protein.

As illustrated in section (v) hereinabove, a composition of the invention may comprise not only one but also two or more polypeptides present as such. The poxvirus may also encode several immunogenic polypeptides, at least one being immunologically cross-reactive with a polypeptide physically present in the composition; or the composition may contain several poxviruses. Advantageously, when several polypeptides are present as such, the compositions of the invention further contain a poxvirus that operatively encodes polypeptides, each of them being two-by-two cross-reactive with the polypeptides physically present. Alternatively, the composition may contain several poxviruses, -each of them encoding a polypeptide cross-reactive with a polypeptide physically present. As understood by a man skilled in the art, a large variety of combinations are possible.

Recombinant pox vectors may be constructed using the basic two-step technique of Piccini et al, (1987) in "Meth. In Enzymology" Acad. Press, San Diego and widely used for any pox vector as described in U.S. Pat. Nos. 4,769,330, 4,772,848, 4,603,112, 5,100,587 and 5,179,993. First, the heterologous DNA sequence to be inserted into the poxvirus is placed under the control of a suitable poxvirus promoter able to direct expression of the sequence in avian or mammalian cells. The expression cassette is then introduced into an *E. coli* plasmid that contains a DNA region homologous to a non-essential locus of the pox vector DNA. The expression cassette is positioned so that it is flanked on both ends by poxvirus homologous DNA sequences. The resulting plasmid is then amplified by growth within *E. coli* and isolated. Second, the isolated plasmid containing the expression cassette to be inserted is transfected into a cell culture, e.g. chick embryo fibroblasts, along with the poxvirus. Recombination between homologous poxvirus DNA present on the plasmid and the viral genome gives a recombinant poxvirus modified by the presence, in a non-essential region of its genome, of the expression cassette containing the heterologous DNA sequence.

For use in the present invention, poxviruses, irrespective of whether they are recombinant or not, may be propagated on mammalian cells such as Vero cells, BHK21 cells and Chick Embryo Fibroblasts (CEF), as described in e.g., Piccini et al, and Taylor et al (supra). Once propagated, the viral particles may be merely harvested and clarified by centrifugation. They may also be purified further according to Joklick et al, Virology (1962) 18:9.

Compositions and/or methods of the invention are useful for both therapeutic and prophylactic purposes. When the immunogenic compound is characteristic of a pathogenic microorganism or a T.A.A., the specific immune response induced upon administration of the compositions or resulting from the methods of the invention, is advantageously protective against the pathogenic microorganism or the tumoral disorder. As a matter of example, there is a need to improve the current influenza vaccine which is not optimally protective in old people. Such pharmaceutical compositions or methods of the invention provide for improved protection over the flu vaccine of the prior art as exemplified in example 6.

Compositions of the invention can be manufactured in a conventional manner. In particular, the compounds can be formulated with a pharmaceutically acceptable diluent or carrier e.g., water or a saline solution such as phosphate buffer saline. In general, a diluent or carrier can be selected on the basis of the mode and route of administration, and standard pharmaceutical practice. Suitable pharmaceutical diluents or carriers as well as pharmaceutical necessities for their use in pharmaceutical formulations are described in *Remington's Pharmaceutical Sciences*, a standard reference text in this field.

A composition of the invention may be administered to any kind of vertebrate, i.a. to mammals or birds, in particular to humans. To this end, one can use any conventional route in use in the vaccine field e.g., via parenteral routes such as the intravenous, intradermial, intramuscular and sub-cutaneous route or mucosal routes such as nasal or oral routes. Especially, for the immunotherapy of cancer it may be useful to administer the pharmaceutical composition intratumorally or into the neighbor lymph nodes.

Compositions comprising a DNA plasmid as immunogenic compound, may advantageously be administered into the epidermis using a special device such as a gene gun or an equivalent device, or by intramuscular route. Taking into account that most of poxvirus are able to infect epidermis cells, it is worth noticing that the composition of the invention and advantageously a composition comprising a DNA plasmid mixed with a poxvirus is suitable for an intradermal or trancutaneous immunization as described by Glenn GM et al, (1998), J. Immunol. 161:3211–3214.

In a general manner, the administration can be achieved in a single dose or repeated at intervals, e.g. repeated twice or more, one or two months apart.

In compositions of the invention, the appropriate dosage of the poxvirus, and the immunogenic compound depends on various parameters understood by skilled artisans such as the vector and the immunogenic compound themselves, the route of administration, the general status of the vertebrate to be vaccinated (weight. age and the like), the type of immune response that is desired and the tumoral or infectious site. An efficient amount of the compounds is such that upon administration, an immune response against the compounds will be induced. For guidance, it is however indicated that the infectious titer (amount of virus able to infect 50% of a cell culture) per dose of the poxvirus may suitably range from $10^3$ to $10^9$, preferably from $10^5$ to $10^8$ CCID50 (Cell Culture Infectious Dose 50). The polypeptide(s) physically present in the composition may amount from 10 $\mu$g to 1 mg, advantageously from 25 to 500 $\mu$g, preferably from 50 to 200 $\mu$g; most preferably, a single dose contains about 50–100 $\mu$g of polypeptide(s). Whenever a DNA plasmid is the immunogenic compound, a convenient dose of DNA plasmid administered may amount from several ng to a few mg depending on the size of the animal giving the composition. In human beings the suitable dose of DNA plasmid per immunization may range from 20 $\mu$g to 2500 $\mu$g as mentioned by Wang R et al (1998), Science, 282, 476–480.

All the documents cited throughout the specification are incorporated by reference.

The invention is further explained and illustrated in the examples by reference to the figures described as follows.

FIGS. 1a and 1b refer to Example 1 and show mean gp160 MN/LAI ELISA antibody titers (log) in guinea-pigs immunized twice by intramuscular route (on days 1 and 29) with vCP205 and/or gp160 MN/LAI 4 µg (1a) or 40 µg (1b).

Figure 2A:
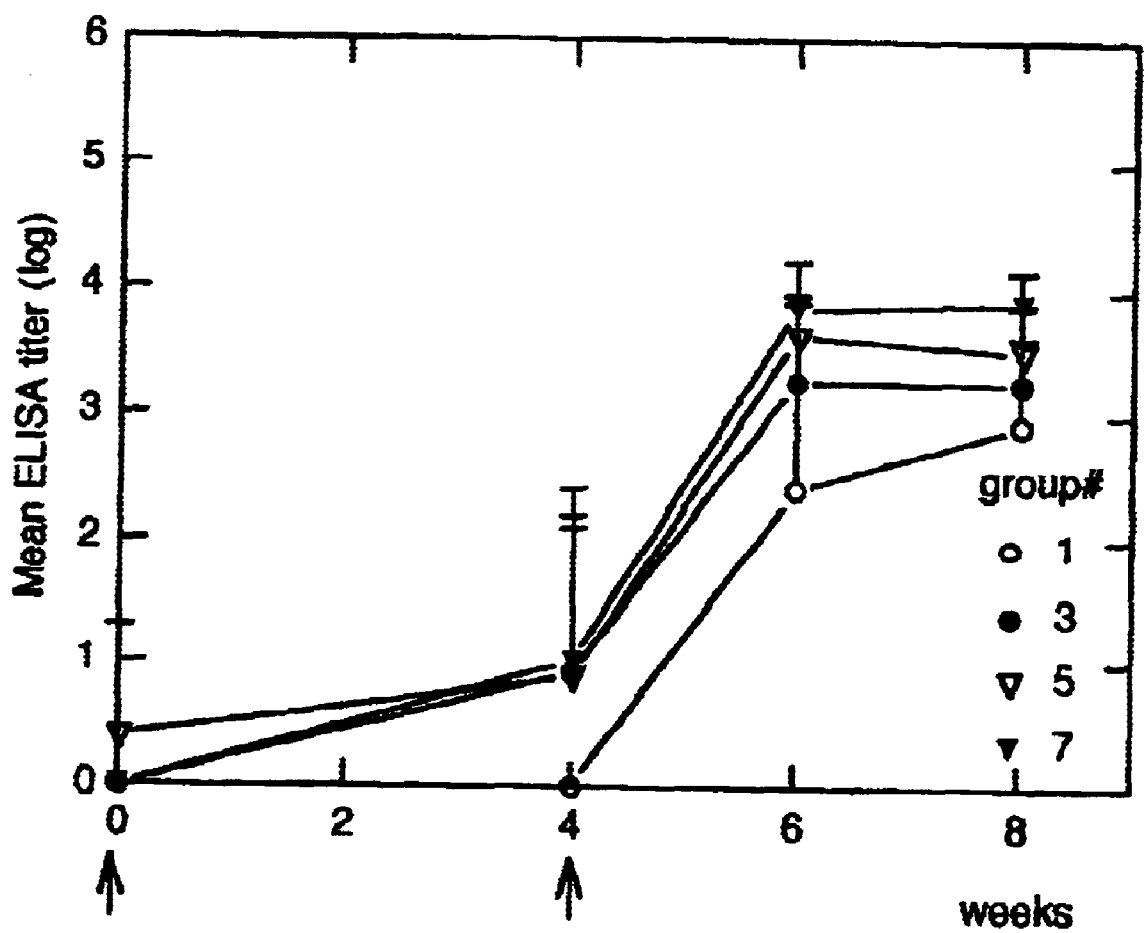

FIGS. 2a and 2b refer to Example 1 and show mean V3 MN ELISA antibody titers (log) in guinea-pigs immunized twice by intramuscular route (on days 1 and 29) with vCP205 and/or gp160 MN/LAI 4 µg (2a) or 40 µg (2b).

In FIGS. 1a and 2a: ○ corresponds to group #1 (D1 and D29 gp160); ● corresponds o group #3 (D1: vCP205 and D29: gp160); ▽ corresponds to group #5 (D1 and D29: vCP205+gp160), and ▼ corresponds to group #7 (D1 and D29: vCP205).

In FIGS. 1b and 2b: ○ corresponds to group #2 (d1 and D29: gp160); ● corresponds to group #4 (D1: vCP205 and D29: gp160); ▽ corresponds to group #6 (D1 and D29: vCP205+gp160); and ▼ corresponds to group #7 (D1 and D29: vCP205).

FIG. 3 refers to Example 2 and shows CPpp antibody titers (log/ml) in guinea-pigs inoculated twice intramuscularly with various doses of vCP205. ● corresponds to group #3 (10^4.8 CCID50); ▼ corresponds to group #5 (10^5.8 CCID50); and ■ corresponds to group #8 (10^6.1 CCID50).

Figure 4A:
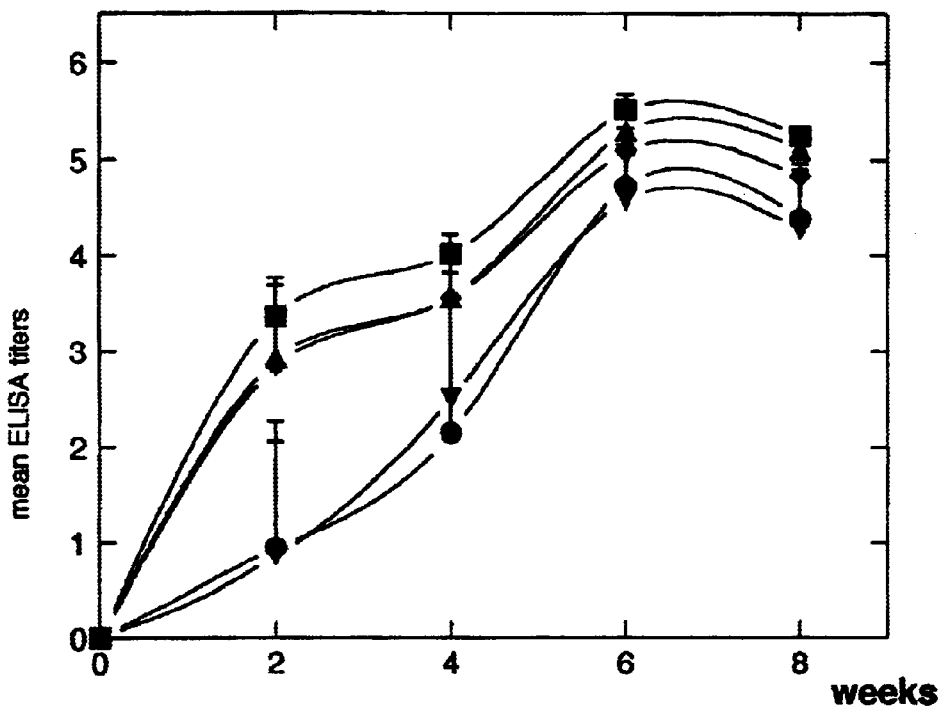
Figure 4B:
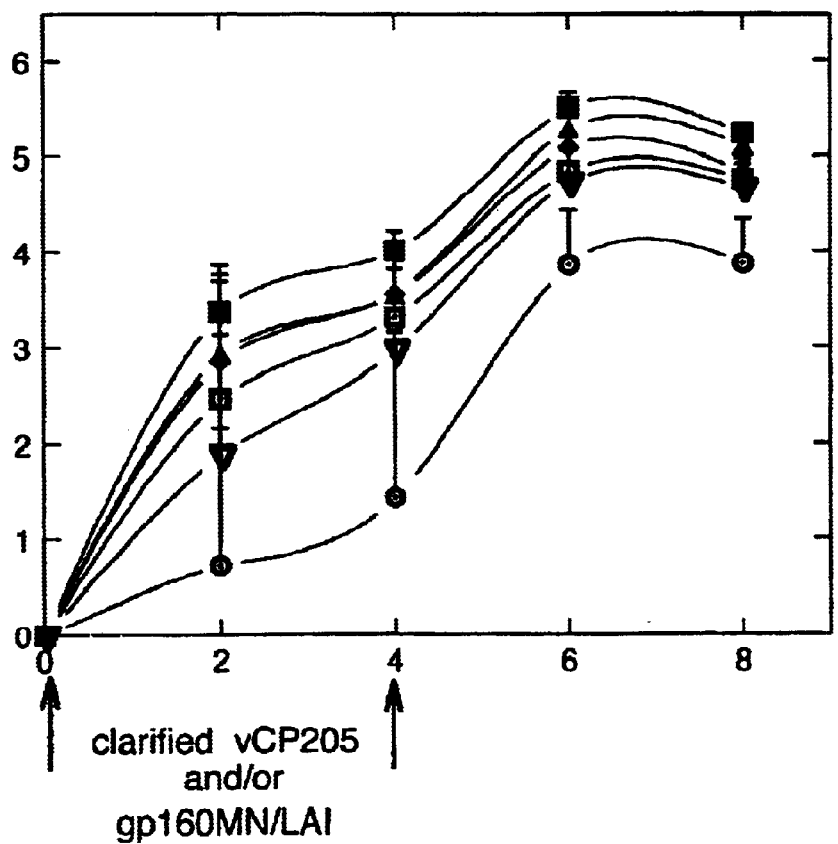

FIGS. 4a and 4b refer to Example 2 and show gp160 MN/LAI ELISA antibody titers (log/ml) in guinea-pigs inoculated twice intramuscularly with various doses of vCP205 and/or gp160 MN/LAI.

In FIG. 4a, ● corresponds to group #1 (40 µg of gp160), ▼ corresponds to group #2 (80 µg of gp160); U corresponds to group #4 (10^4.8 CCID50 of vCP205+40 µg of gp160); ▲ corresponds to group #6 (10^5.8 CCID50 of vCP205+40 µg of gp160 mixed together); and ◆ corresponds to group #7 (10^5.8 CCID50 of vCP205+40 µg of gp160 injected separately).

In FIG. 4b, ○ corresponds to group #3 (10^4.8 CCID50 of vCP205), ▽ corresponds to group #5 (10^5.8 CCID50 of vCP205), □ corresponds to group #8 (10^6.1 CCID50 of vCP205), ■ corresponds to group #4 (10^4.8 CCID50 of vCP205+40 µg of gp160), ▲ corresponds to group #6 (10^5.8 CCID50 of vCP205+40 µg of gp160 mixed together),◆ corresponds to group #7 (10^5.8 CCID50 of vCP205+40 µg of gp160 injected separately).

Figure 5:
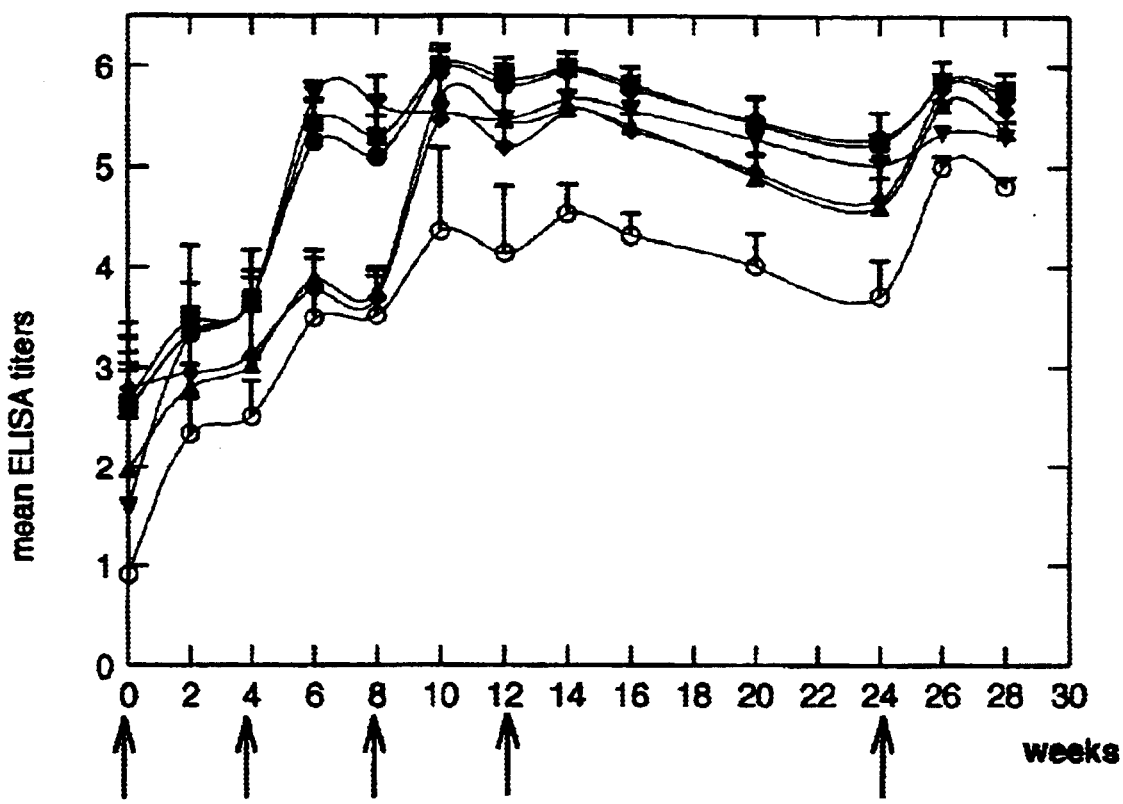
Figure 6:
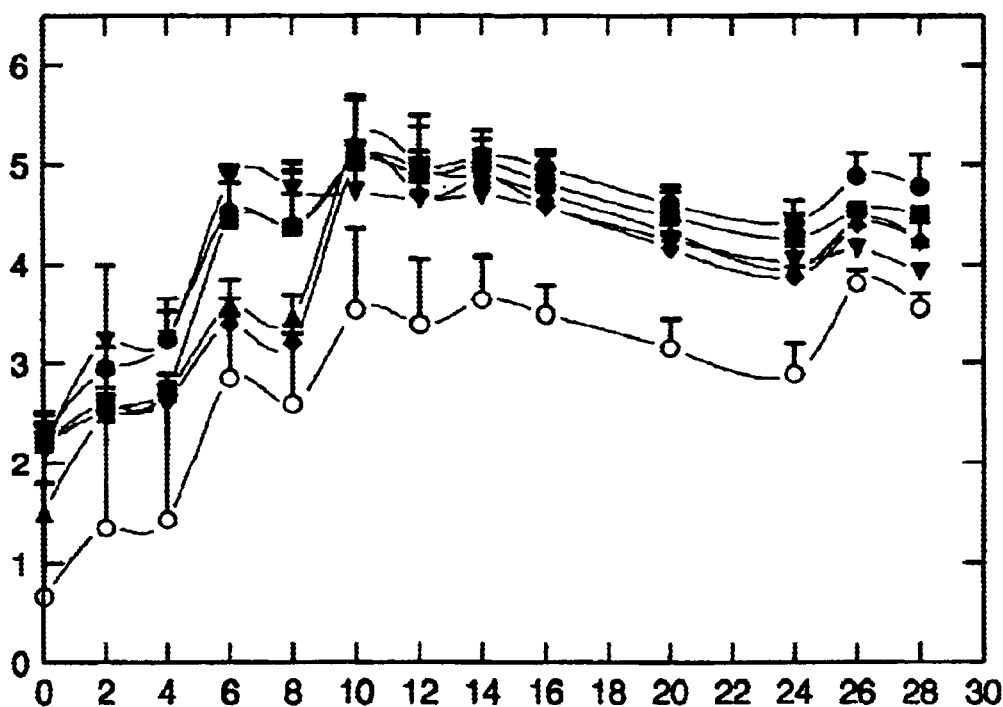
Figure 7:
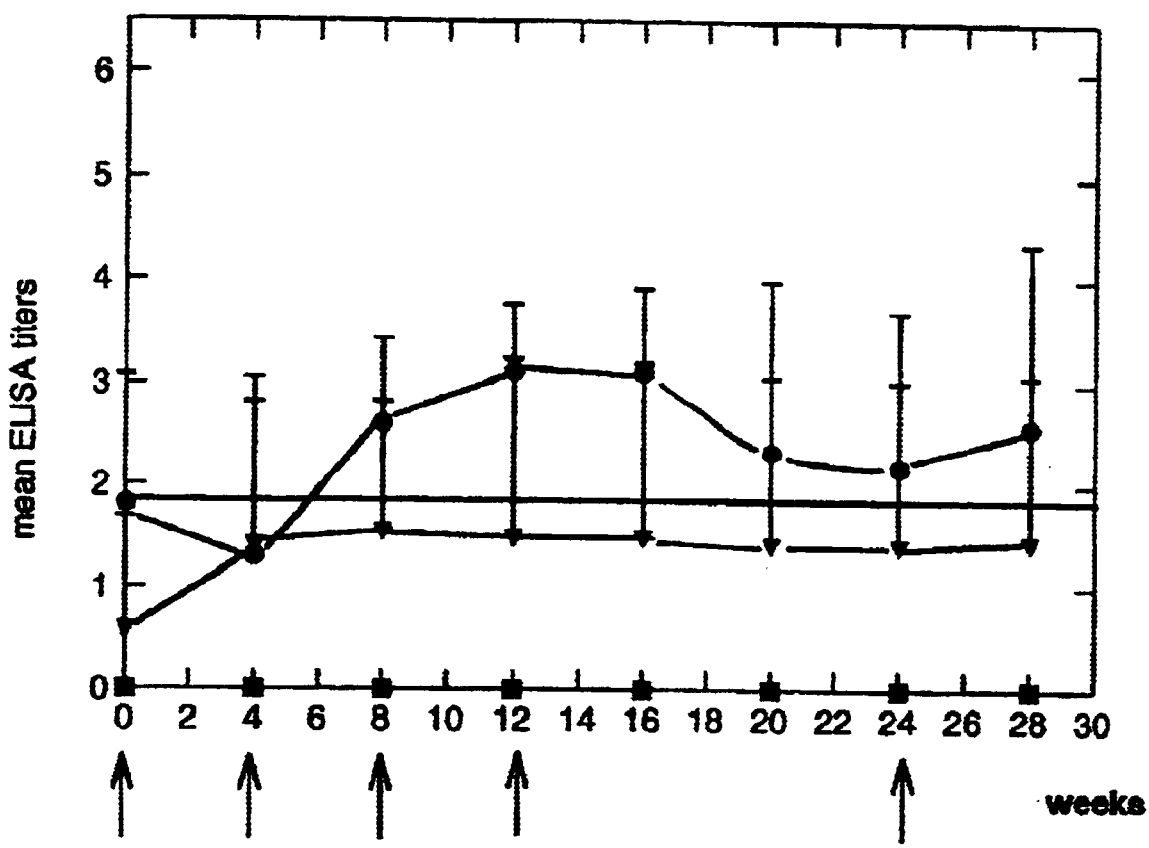
Figure 8:
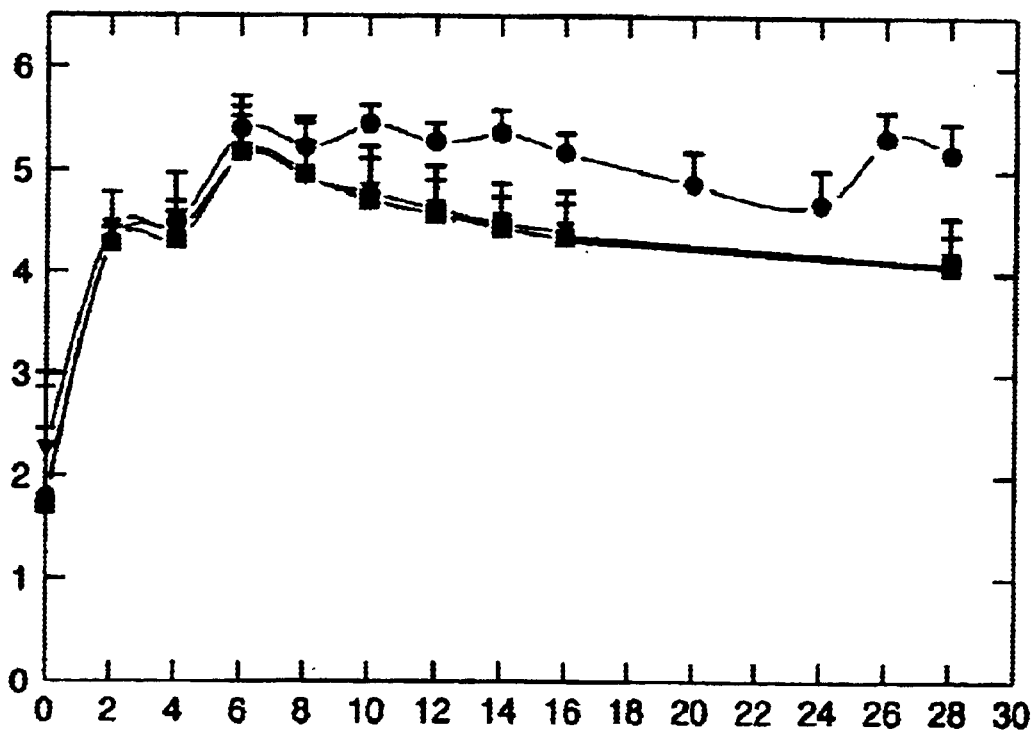

FIGS. 5 to 8 refer to Example 3 and show the mean ELISA antibody titers (log/ml) in macaques immunized intramuscularly with $10^{6.5}$ CCID50 vCP205 and/or 100 µg gp160 MN/LAI adjuvanted or not (FIG. 5 gp160 ELISA antibody; FIG. 6: V3 MN ELISA antibody; FIG. 7: p24 LAI ELISA antibody; FIG. 8: CPpp ELISA antibody). ◆ corresponds to group #1; ▽ corresponds to group #2; ○ corresponds to group #3; and ▼ corresponds to group #4. (■ is irrelevant).

Figure 9:
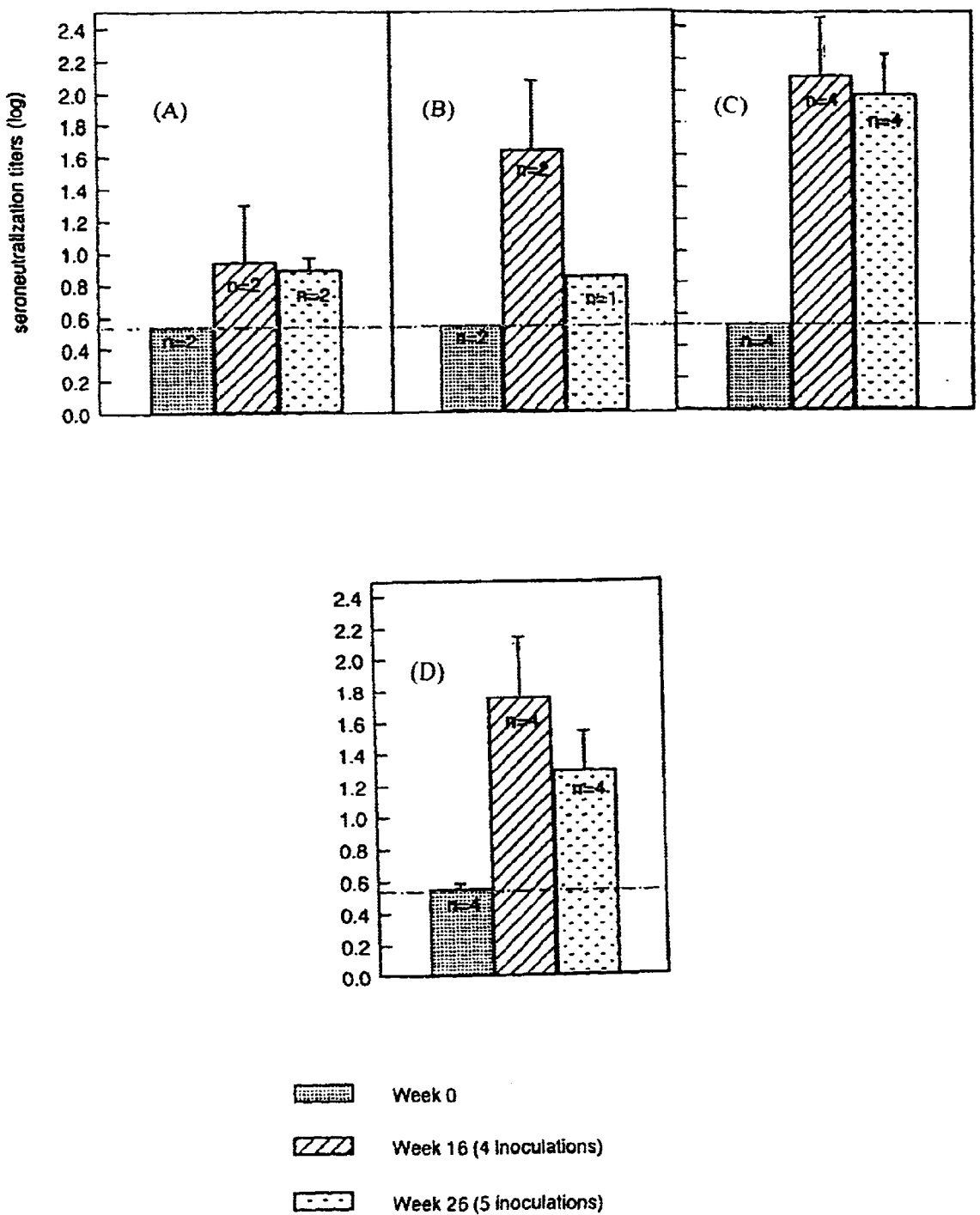

FIG. 9 refers to Example 3 and shows the HIV MN seroneutralizing antibody titers (log) in macaques immunized five times intramuscularly with $10^{6.5}$ CCID50 vCP205 and/or 100 µg gp160 MN/LAI adjuvanted or not at weeks 0 (square-dotted box), 16 (hatched box) and 26 dotted box). Schemes A to D correspond respectively to groups #1 to #4.

FIGS. 10a and 10b refer to Example 4 and show ELISA CPpp antibody (1a) and gp160 MN/LAI antibody (1b) mean titers in guinea-pigs primed intramuscularly with a mixture of gp160 MN/LAI (5 µg) and different doses of crude or purified CPpp, then boosted with 5 µg of gp160 MN/LAI. ○ corresponds to group #1; ● corresponds to group #2; ▽ corresponds to group #3; ▼ corresponds to group #4; and □ corresponds to group #5.

Figure 11A:
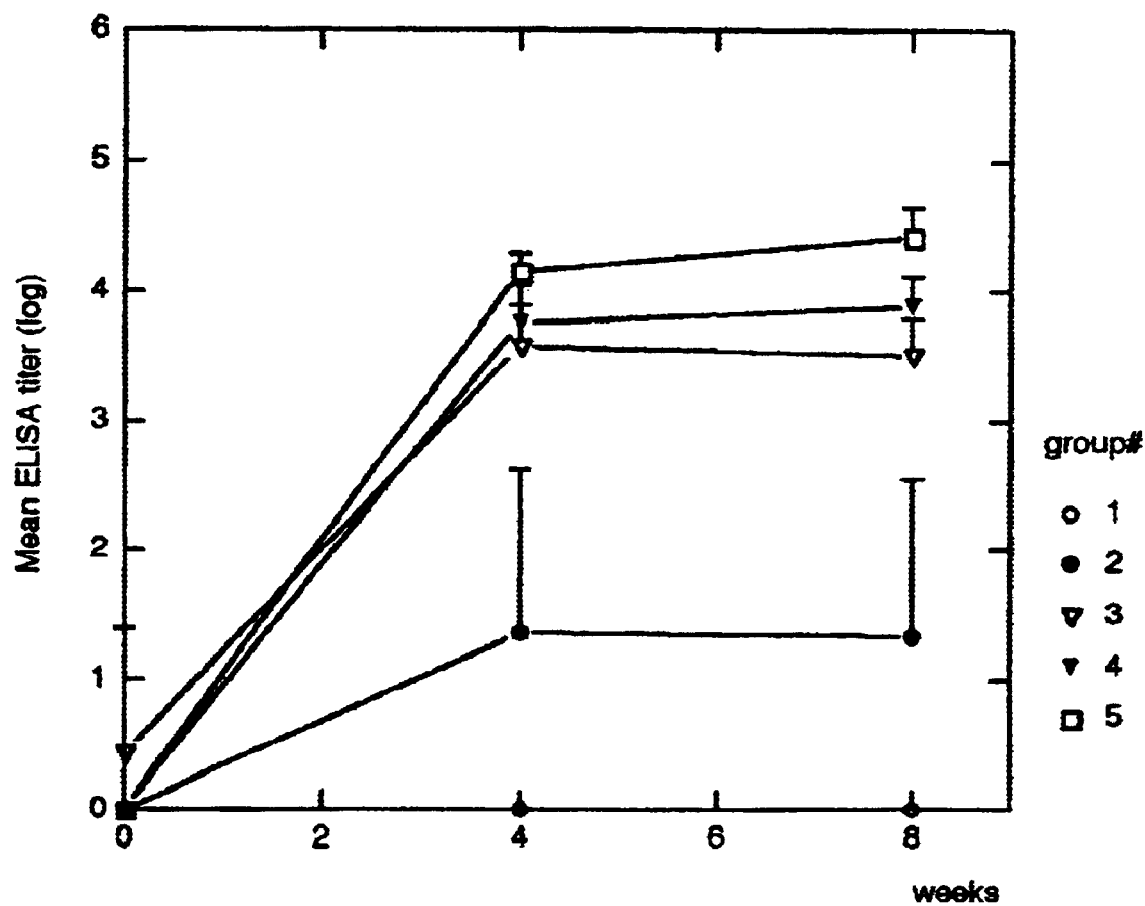

FIGS. 11a and 11b refer to Example 5 and show ELISA IgG CPpp antibody (2a) and gp160 MN/LAI antibody (2b) mean titers in guinea-pigs primed intramuscularly with a mixture of gp160 MN/LAI (5 µg) and different fractions of ALVAC-Luc (vCP297), either inactivated or not, then boosted (week 4) with 5 µg of gp160 MN/LAI. ○ corresponds to group #1; ● corresponds to group #2; ▽ corresponds to group #3; ▼ corresponds to group #4; and □ corresponds to group #5.

Figure 12:
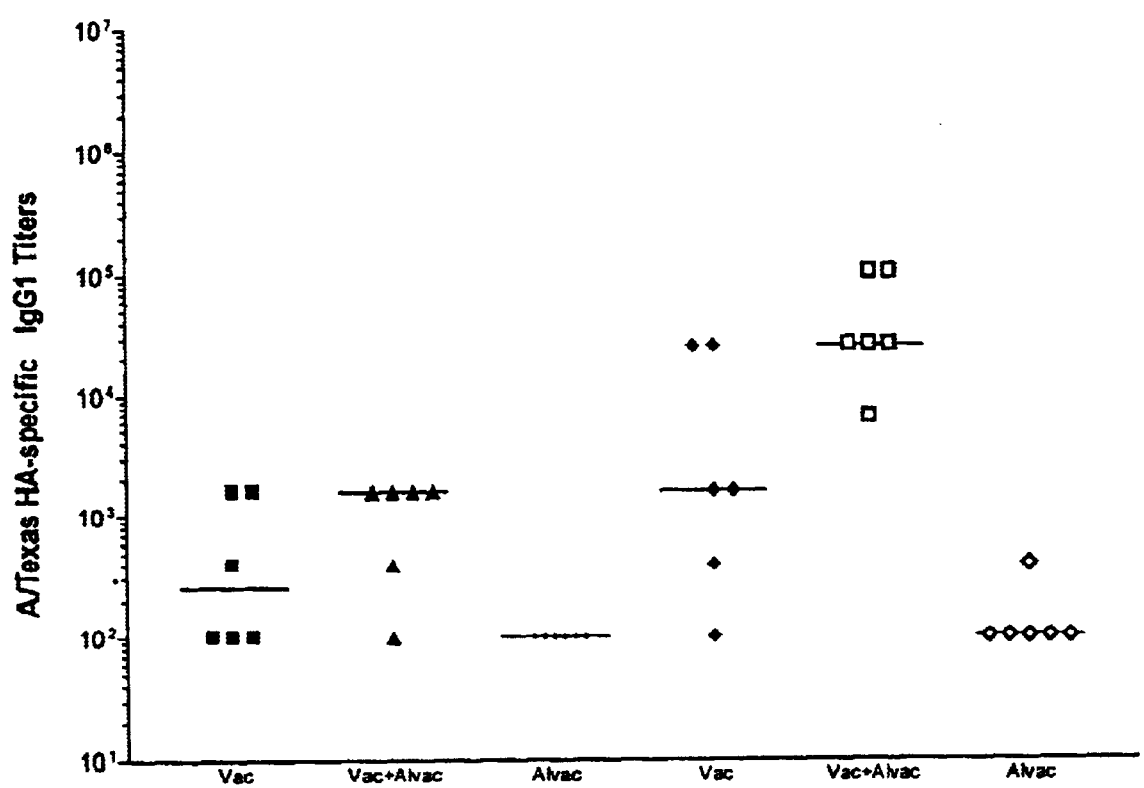
Figure 13:
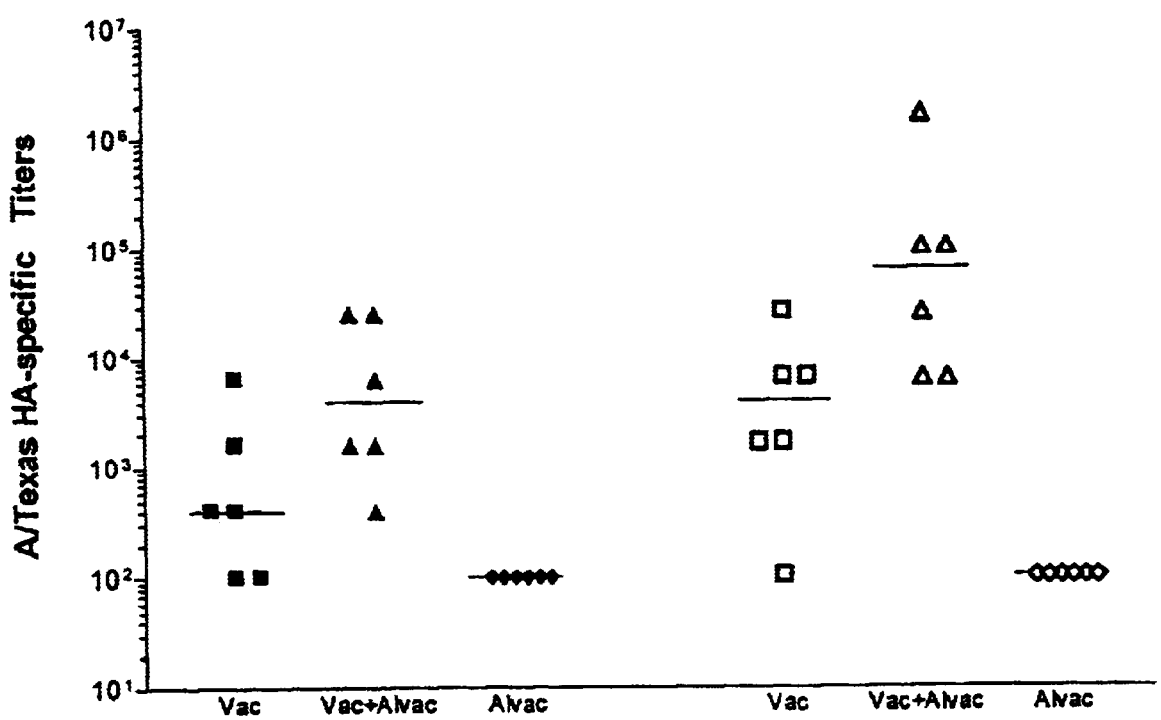

FIGS. 12 and 13 refer to example 6 and show respectively the IgG1 and IgG2a ELISA antibody titers specific for A/Texas in each individual aged DBA/2 mice immunized twice with either 3 µg of A/Texas (group 1), $2 \times 10^7$ CCID50 of CPpp and 3 µg of A/Texas (group 2) or $2 \times 10^7$ CCID50 of CPpp (group 3). ■ and ◆ correspond to mice of group 1 respectively after one and two immunizations. ▲ and □ correspond to mice of group 2 respectively after one and two immunizations. ◆ and ◇ correspond to mice of group 3 respectively after one and two immunizations.

Figure 14:
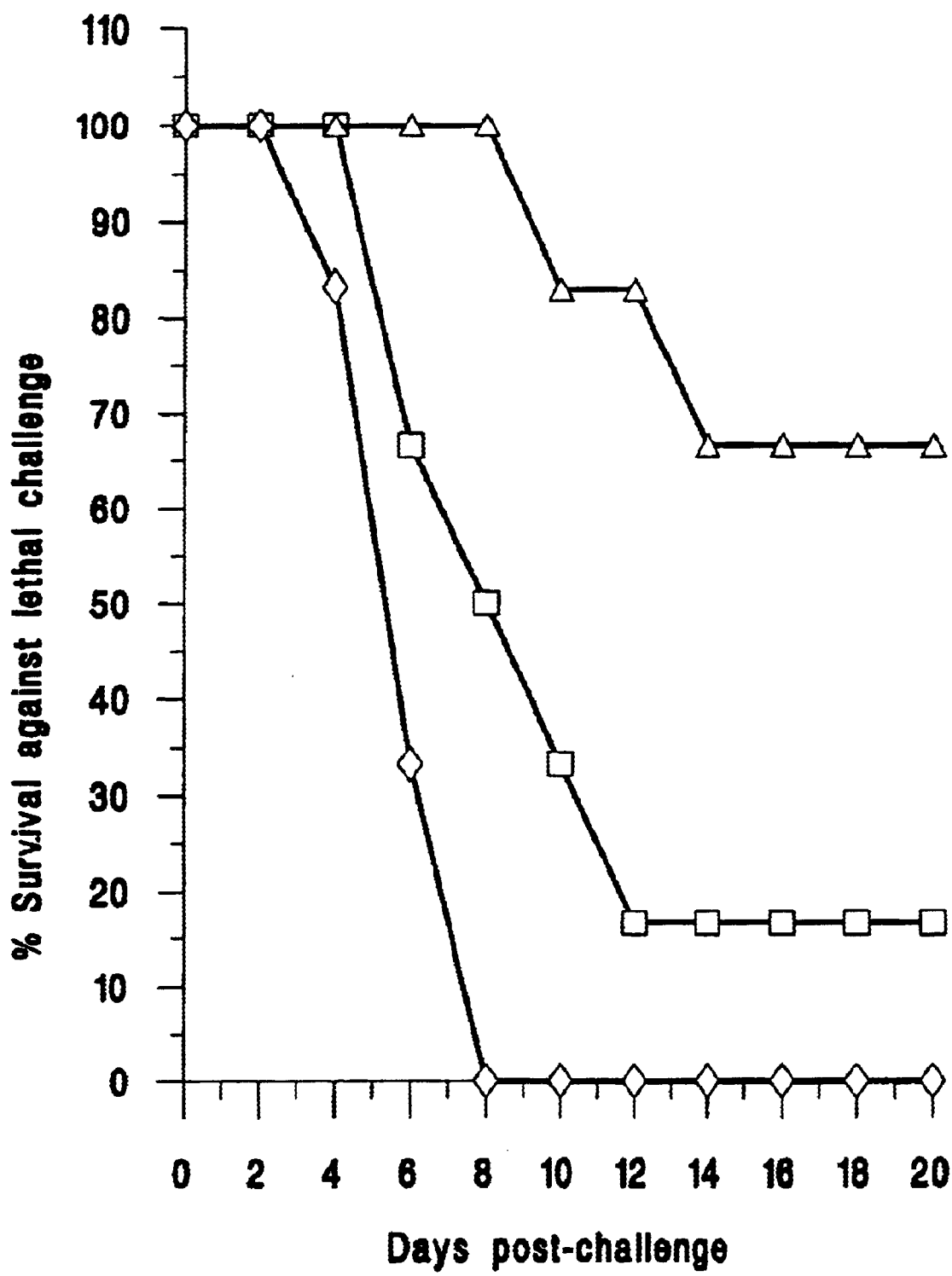

FIG. 14 refers to example 6 and shows the survival curves of the 3 immunized groups after a lethal challenge with A/Taïwan. Δ corresponds to group 1; □ corresponds to group 2; ◆ corresponds to group 3.

Figure 15:
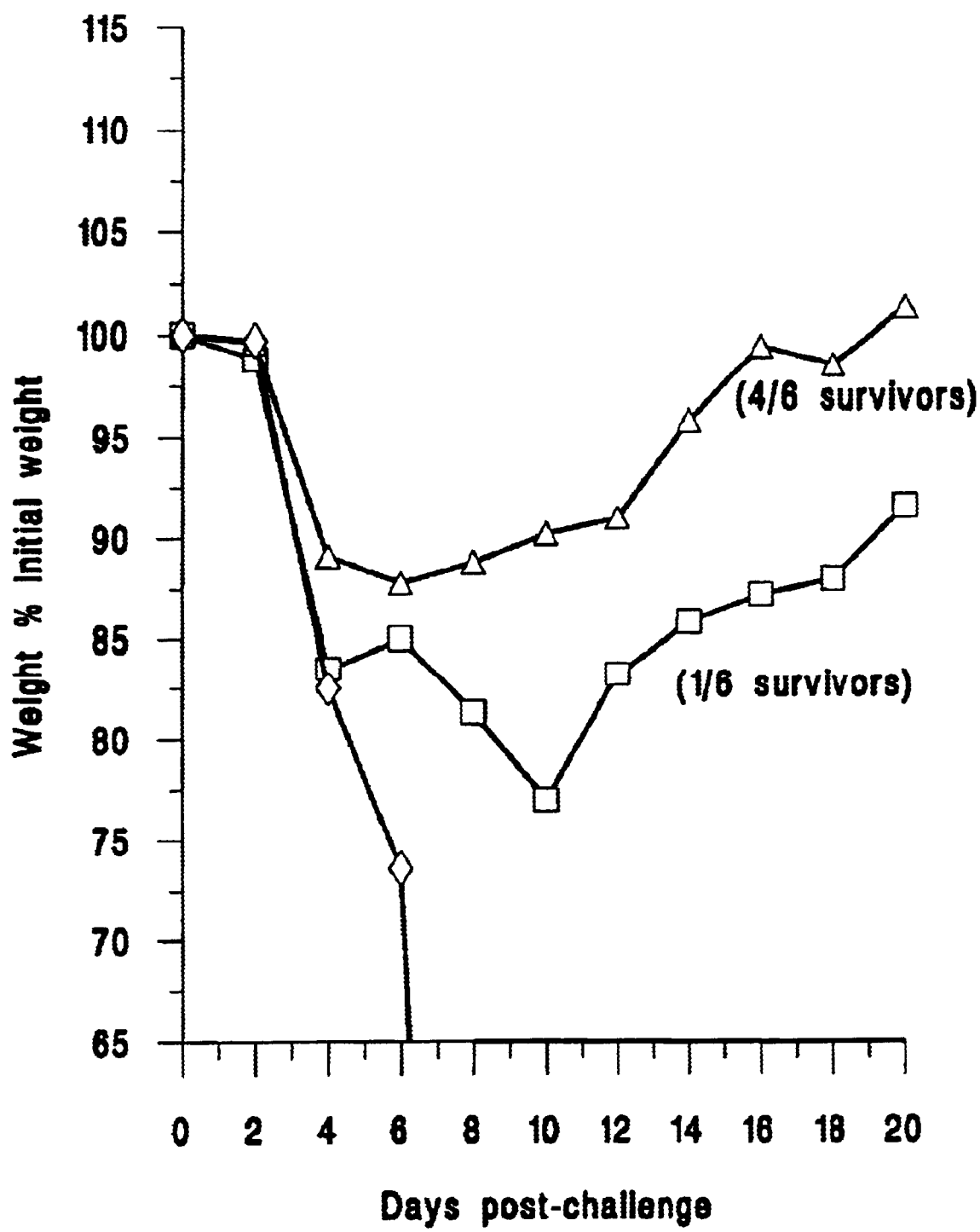

FIG. 15 refers to example 6 and shows the morbidity curves of the 3 immunized groups after a lethal challenge with A/Taïwan. Δ corresponds to group 1; □ corresponds to group 2; ◆ corresponds to group 3.

Example 1

Simultaneous Immunization With ALVAC-HIV (vCP205) and gp160 MN/LAI in Guinea Pigs 1A—vCP205 Preparation vCP205, an ALVAC pox vector capable of expressing HIV proteins, is described in Example 14 of WO 95/27507. Briefly, it contains a first heterologous sequence encoding the env gp120 MN+the transmembrane region of LAI gp41, and a second sequence encoding LAI (gag+protease); these sequences are inserted in the C3 locus and placed under the control of promoters H6 and I3L.

Clarified vCP205 was produced on chick embryo fibroblasts in DMEM—Ham F12 medium without serum, harvested in lactoglutamate and clarified by centrifulgation. The preparation used hereinafter has a mean titer of $10^{8.5}$ $CCID_{50}$/ml on QT35 cells.

Purified vCP205 was produced as described above and further purified according to Jokick et at, (supra). The VCP205 preparation in phosphate buffer saline (PBS) 20 mM pH 7.2 (in the absence of $Mg^{++}$ and $Ca^{++}$) as used hereinafter, has a mean titer of in $10^{8.8}$ $CCID_{50}$/ml on QT35 cells.

1B—gp160 MN/LAI Preparation

A recombinant vaccinia virus vector, VVTG9150, is used for gp160 production. VVTG9150 operatively encodes a hybrid, soluble HIV-1 gp160 in which the gp120 moiety derives from HIV-1 MN and the gp41 trans-membrane part comes from the LAI isolate. The DNA sequences corresponding to these two compounds are fused together using an artificial SmaI restriction site, which modifies neither the gp120, nor the gp41 amino acid sequence. The construction of the two partners is briefly described as follows.

The sequence encoding the MN gp120 was amplified from cells SupT1infected with HIV-MN, using the PCR technique with oligonucleotides which introduce a SphI and SmaI restriction sites respectively located immediately downstream of the sequence encoding the leader peptide and upstream of the cleavage sites located between gp120 and gp41.

The sequence encoding the LAI gp41 was produced as follows: The complete HIV-1 LAI env coding sequence was placed under the control of the vaccinia pH5R promoter. Several modifications were introduced into this encoding sequence. First a SphI restriction site was created immediately downstream of the sequence encoding the leader peptide, without altering the amino acid sequence. Second, a SmaI restriction site was created immediately upstream of the sequence encoding the cleavage sites between gp120 and gp41, without altering the amino acid sequence. Third, the two cleavage sites in position 507–516 (amino acids numbered according to Myers et al, In: Human retroviruses and AIDS (1994) Los Alamos National Lab. (USA)) were mutated (original sequence KRR . . . REKR mutated into QNH . . . QEHN). Fourth, the sequence encoding the transmembrane hydrophobic peptide IFIMIVGGLVGLRIV-FAVLSIV (amino acids 689–710 in Myers et al (supra)) was deleted. Fifth, a stop codon was substituted for the second E codon of the sequence encoding PEGIEE (amino acids 735–740 in Myers et al (supra)) i.e., the 29th amino acid of the intracytoplasmic domain. The plasmid in which the LAI sequence was inserted between vaccinia virus thymidine kinase (TK) gene homologous regions, was cut with SphI and SmaI and further ligated with the MN gp120 sequence. VVTG9150 was then constructed b) conventional homologous recombination and propagated for MN/LAI gp160 expression according to the conventional method used for vCP205 on BHK21 cells. The protein was purified by immunoaffinity chromatography.

1C—Experimental Procedure

Guinea pigs were submitted to immunization protocols as described in Table 1 hereinafter.

TABLE 1

| Group # | Inoculation days | |
|---|---|---|
| (Guinea-pig) | D1 | D29 |
| 1 (1, 2, 3, 4, 5) | 4 µg gp160 | 4 µg gp160 |
| 2 (6, 7, 8, 9, 10) | 40 µg gp160 | 40 µg gp160 |
| 3 (11, 12, 13, 14, 15) | $10^{6.1}$ CCID50 ALVAC-HIV | 4 µg gp160 |
| 4 (16, 17, 18, 19, 20) | $10^{6.1}$ CCID50 ALVAC-HIV | 40 µg gp160 |
| 5 (21, 22, 23, 24, 25) | $10^{6.1}$ CCID50 ALVAC-HIV + 4 µg gp160 | $10^{6.1}$ CCID50 ALVAC-HIV + 4 µg gp160 |
| 6 (26, 27, 28, 29, 30) | $10^{6.1}$ CCID50 ALVAC-HIV + 40 µg gp160 | $10^{6.1}$ CCID50 ALVAC-HIV + 40 µg gp160 |
| 7 (31, 32, 33, 34, 35) | $10^{6.1}$ CCID50 ALVAC-HIV | $10^{6.1}$ CCID50 ALVAC-HIV | each dose was administered intramuscularly under a final volume of 1.2 ml (0.6 ml in each thigh). When vCP205 and gp160 were both administered, these two products were mixed together before.

Serological analyses were carried out with blood samples collected on days 0 (one day before the first immunization), 28. 43 and 57. Antibodies to HIV gp160 glycoprotein and V3 peptide titrated by ELISA as follows:

Maxisorp F96 NUNC plates were coated for 1 hour at 37° C., then overnight at 4° C. with one of the following antigens, diluted in 0.1 M carbonate buffer, pH 9.6:130 ng per well of purified gp160 MN/LAI; 200 ng of V3 peptide from HIV MN.

Plates were then blocked for 1 hour at 37° C. with 150 µl of phosphate buffered saline (PBS) pH 7.1–0.1% Tween 20–5% (w/v) powdered skim milk, (PBS-Tween-milk). All next incubations were carried out in a final volume of 100 µl, followed by 3 or 4 washings with PBS, pH 7.1–0.1% Tween 20.

Serial threefold dilutions of the sera, ranging from 1/100 to 1/24300 or 1/1000 to 1/243000, in PBS-Tween-milk, were added to the wells and incubated for 90 min at 37° C. After washings (3 times), anti-guinea-pig IgG peroxydase conjugate (Sigma, rabbit IgG fraction) was diluted at 1/3000 in PBS-Tween-milk, added to the plates and incubated for another 90 min at 37° C. The plates were further washed (4 times) and incubated in the dark for 30 min at room temperature with O-phenylenediamine dihydrochloride (Sigma) at 1.5 mg/ml in 0.05 M phosphate citrate buffer, pH 5.0 containing 0.03% sodium perborate (Sigma). The reactions were stopped with 50 µl of 4N $H_2SO_4$.

The optical density (OD) was measured at 490–650 nm with an automatic plate reader (Vmax, Molecular Devices). The blanks (mean value) were substracted to the data and duplicate values averaged. The antibody titers were calculated for the OD value range of 0.2 to 1.3, from the regression curve of a standard hyperimmnune guinea-pig serum specific for both gp160 and V3 antigens, present on each ELISA plate.

The titer of the standard serum had been previously determined according to the formula:

$$Titer = \log \frac{OD_{490-650} \times 10(OD \text{ value range: } 0.2 \text{ to } 1.3)}{1/\text{dilution}}.$$

ID—Serological Results

Averaged titers for each group of guinea pigs are presented in FIGS. 1 (gp160 antibody titers) and 2 (V3 antibody titers).

Comparison of the anti-HIV antibody responses induced by gp160 alone (groups #1 and #2), vCP205 alone (group #7), and combination of both antigens (groups #5 and #6)

Antibody Responses to gp160

The lowest responses were observed, after both the primary and booster immunizations, in guinea pigs that received 4 µg of gp160 (group #1). With 40 µg of gp160 (group #2), humoral responses were much more elevated: only one inoculation was required for all animals to seroconvert, versus two with the 4 µg dose; and the mean antibody titers to V3 and gp160 were higher in group #2 than in group #1 (>+1 log higher on week 6).

vCP205 ($10^{6.1}$ CCID50) injected alone (group #7) elicited anti-HIV antibodies at comparable but lower levels than those induced by gp160 alone at 40 µg, especially after the booster injection (difference in mean titers ≈−0.4 log on week 6).

Mixing vCP205 with 4 µg of gp160 (group #5) was not found to significantly enhance the antibody response comparatively to vCP205 alone. Conversely, and of great interest, two immunizations with the combination vCP205 plus gp160 at 40 µg (group #6) induced the best antibody titers, higher than those raised by vCP205 alone (group #7) (raise of mean ELISA titers ≈+0.8 log on week 6) and, in lesser extent, by 40 µg of gp160 alone (group #2)(≈0.4 log on week 6).

Antibody Responses to V3

Although the antibody titers raised against the V3 domain were, as previously observed, lower than those induced against whole gp160, the reactivity pattern to V3 was similar to that obtained to gp160. In particular, the (vCP205 plus 40 µg of gp160) combination proved to be the best immunogen, whereas the 4 µg dose of gp160 injected alone was the worst.

Comparison of the anti-HIV antibody responses induced by the mixture of vCP205 plus gp160 (groups #5 and #6) and by a prime (vCP205)/boost (gp160) immunization regimen (groups #3 and #4).

As observed in previous tests, a clear priming effect of vCP205 on the anti-HIV humoral responses following a boost with gp160 (at either 4 or 40 µg) was found. Nonetheless, animals immunized according to this prime/boost regimen displayed lower responses to V3 than those inoculated with two injections of the mixture vCP205 plus gp160 (using 4 or 40 µg of gp160). Similar differences were seen when anti-gp160 responses were considered, but only with 40 µg of gp160.

Noticeably, the prime/boost immunization using: (i) 40 µg of gp160 (group #4) gave antibody levels equivalent to those elicited by two inoculations of gp160 alone at 40 µg (group #2); or (ii) 4 µg of GP160 (group #3) raised antibody titers similar to or lower than those induced by two injections of vCP205 (group #7).

General Conclusion

Immunogenicity of the different combinations of ALVAC-HIV vCP205 and/or gp160 MN/LAI evaluated in the present study in guinea pigs can be classified as followed:

gp160 (4 µg)<prime vCP205/boost gp160 (4 µg)=vCP205 vCP205+gp160 (4 µg=prime vCP205/boost gp160 (40 µg) gp160 (40 µg)<vCP205+gp160 (40 µg).

In particular, these results revealed that two co-injections of vCP205 and gp160 can induce higher anti-HIV serological responses (to V3 and gp160) than two inoculations of either vCP205 or gp160 alone, or than a prime (vCP205)/boost (gp160) immunization. Such an enhancing effect was observed mainly when vCP205 was combined with a high dose of gp160 (40 µg) but not with a lower one (4 µg).

Example 2

Analysis of the Enhancing Effect of a Mixture vCP205+pg160 MN/LAI on the Antibody Response to gp160 MN/LAI in Guinea-pigs The experiment reported in Example 2 were performed in guinea-pigs (i) to confirm the ability of the mixture gp160 MN/LAI plus vCP205 to stimulate the antibody response to gp160, as previously observed in Example 1; (ii) to determine whether this enhancement results from a simple additive or rather a synergistic effect between the two immunogens; and (iii) to evaluate whether such an effect can be obtained when the two products are inoculated simultaneously at distinct sites or only when they are mixed.

2A—vCP205 Preparation was Achieved as Described in Example 1A Hereinabove
2B—gp160 Preparation was Achieved as Described in Example 1B Hereinabove
2C—Experimental Procedures Thirty-nine guinea pigs distributed in eight groups received vCP205 and/or gp160 doses as stated in Table 2.

TABLE 2

| | | ALVAC-HIV (vCP205) (CCID50) | | |
|---|---|---|---|---|
| | | 0 | $10^{4.8}$ | $10^{5.8}$ | $10^{6.1}$ |
| gp160 (µg) | 0 | | # 11 to 14 mixed | # 21 to 24 mixed | # 36 to 40 |
| | 40 | # 1 to 5 | # 15 to 19 | # 25 to 30 separately # 31 to 35 | |
| | 80 | # 6 to 10 | | | |

Each guinea pig received intramuscularly two identical injections (each under a volume of 1.2 ml), one month apart. The viral vector and the mixtures were administered in both thighs, whereas gp160 alone was administered in the right fore leg.

Serological analyses were carried out with blood samples collected on days 1, 15, 28, 43 and 57. Antibodies to HIV gp160 MN/LAI glycoprotein and to non-recombinant purified canary pox (CPpp) were titrated by ELISA as described in Example 1C. To this end, 500 ng of CPpp/well were used as well as a standard hyperimmune guinea-pig serum for CPpp.

2D—Serological Results

Anti-CPpp Antibody Response

The antibody response elicited against CPpp was measured in the three groups of guinea pigs inoculated with $10^{4.8}$, $10^{5.8}$ or $10^{6.1}$ CCID50 of ALVAC-HIV (vCP205) alone (groups #3, #5 and #8, respectively). The mean titers of each group are presented in FIG. 3.

The doses of $10^{4.8}$ and $10^{5.8}$ CCID50 of vCP205 raised similar anti-CPpp antibody levels, which proved to be lower than those induced by the dose of $10^{6.1}$ CCID50 of ALVAC-HIV, mostly after the first injection (difference in mean titers of ~−0.7 log on week 4).

Anti-gp160 MN/LA! Antibody Response

The antibody response to gp160 MN/LAI was measured in all immunized animals. The mean titers of each group are represented in FIGS. 4a and 4b.

When the groups of guinea pigs were globally compared by variance analysis, a significant difference between immunogens was observed in the antibody response elicited against gp160 ($p<0.0005$).

Injections of either gp160 MN/LAI at 40 or 80 µg (groups #1 and #2) or ALVAC-HIV (vCP205) at $10^{5.8}$ or $10^{6.1}$ CCID50 (groups #5 and #8) were found to induce close anti-gp160 antibody levels which proved to be statistically identical along the study. ALVAC-HIV (vCP205) at the dose of $10^{4.8}$ CCID50 (group #3) appeared to raise lower antibody responses, the difference in mean titers with groups #1, #2, #5 and #8 ranging from −0.4 to 1.8 log during the serology, but statistical significance was evidenced only with group #8.

These results suggested that the gp160-specific humoral response elicited by the HIV protein at 40 to 80 µg or the recombinant ALVAC-HIV (vCP205) at $10^{5.8}$ or $10^{6.1}$ CCID50 had reached its maximum. However, mixture $10^{4.8}$ CCID50 vCP205 plus 40 µg gp160 (group #4) was found to induce elevated antibody titers which proved to be significantly higher than those raised (i) by vCP205 alone at $10^{4.8}$, $10^{5.8}$ or $10^{6.1}$ CCID50 (difference in mean titers ranging from +0.5 to +2.6 log), and (ii) by gp160 alone at 40 or 80 µg (difference in mean titers ranging from +0.8 to +2.5 log).

The anti-gp160 antibody levels induced by the mixture vCP205 at $10^{5.8}$ CCID50 plus 40 µg gp160 (group #6) also appeared to be high and did not significantly differ from those elicited in group #4 (mixture with vCP205 at $10^{4.8}$ CCID50). Moreover, the simultaneous injection of $10^{5.8}$ CCID50 vCP205 and 40 µg gp160 either mixed (group #6) or injected separately (group #7) gave similar increased antibody responses, as confirmed statistically.

Whether or not the strongest anti-gp160 antibody responses observed with the three combinations of vCP205 and gp160 (groups #4, #6 and #7) resulted from a simple additive or rather a synergistic effect between both immunogens was difficult to assess. In an attempt to address this issue, the mean ELISA titers measured experimentally for each combination were compared to the estimated titers that would result from an additive effect between gp160 and vCP205. As shown in Table 4, the titers measured for the mixture with vCP205 at $10^{4.8}$ CCID50 (group #4) were found to be higher than the theoretical additive titers, the ratio "measured titer/theoretical additive titer" ranging from 5.4 to 165.5 along the serology. This ratio was also above 1 albeit never exceeding 10, for the group receiving the mixture with vCP205 at $10^{5.8}$ CCID50 (group #6). This was also true when gp160 was administered separately to vCP205 at the same dose (group #7), but only after the primo immunization (weeks 2 and 4).

These results suggested that a synergism between ALVAC-HIV (vCP205) and gp160, potentiating the antibody response to gp160, can occur. Such an effect would also take place when both immunogens are injected separately, although apparently less efficiently.

General Conclusion

The ability of the combination of gp160 MN/LAI (40 μg) and ALVAC-HIV (vCP205) ($10^{4.8}$ or $10^{5.8}$ CCID50) to stimulate the humoral response to gp160 MN/LAI in guinea pigs was confirmed. The antibody levels elicited against the HIV protein by these mixtures were indeed increased comparatively to those obtained by each immunogen at either a similar or a two-fold (or more) higher dose (i.e. gp160 at 40 or 80 μg or ALVAC-HIV at $10^{4.8}$, $10^{5.8}$ or $10^{6.1}$ CCID50).

This stimulating effect seemed to result from a synergistic rather than an additive phenomenon, and could also occur at distance when both antigens were injected at distinct sites.

Example 3

Comparison of the Immune Response Induced in Rhesus Macagues Either by a Mixture of vCP205+ gp160 MN/LAI or a Prime Boost Immunization vCP205/gp160 MN/LAI in Aluminum Hydroxide Al (OH)$_3$(Alum)

3A—vCP205 Preparation was Achieved as Described in Example 1A Hereinabove

3B—gp160 Preparation was Achieved as Described in Example 1B Hereinabove

3C—Experimental Procedure

Thirteen rhesus macaques (*Macaca mulatta*) were immunized according to the immunization protocols as shown in Table 3.

TABLE 3

| Macaques Group # | Sex and number | Immunizations (Weeks) | | | | |
|---|---|---|---|---|---|---|
| | | W0 | W4 | W8 | W12 | W24 |
| 1 | F1, F2 | gp160 | gp160 | gp160 | gp160 | gp160 |
| 2 | F4, F5, M6 | gp160 + alum | gp160 + alum | gp160 + alum | gp160 + alum | gp160 + alum |
| 3 | M11, F12, M13, F18 | AL-VAC-HIV + gp160 | ALVAC-HIV + gp160 | ALVAC-HIV + gp160 | ALVAC-HIV + gp160 | ALVAC-HIV + gp160 |
| 4 | F19, F20, F21, M22 | AL-VAC-HIV | ALVAC-HIV | gp160 + alum | gp160 + alum | gp160 + alum |

F: female; M: male.

Macaques were administered doses intramuscularly in one thigh (right or left alternatively), under a final volume of 1 ml, comprising $10^{6.5}$ CCID50 vCP205, 100 μg gp160 and/or 0.3 mg alum.

Blood samples were collected every two weeks, starting on week 0 (first immunization week).

Antibodies to HIV gp160 MN/LAI glycoprotein, V3 MN peptide, p24 LAI and CPpp were titrated by ELISA (FIGS. 5 to 8) as described in Example 1C. Reagent dosages were as follows: gp160 MN/LAI:130 ng/well; V3 MN peptide:200 ng/well; p24 LAI: 130 ng/well; and CPpp:500 ng/well.

Two different peroxydase conjugates were used, diluted in PBS-Tween-milk, depending on the coating antigen:
for the gp160 MN/LAI, V3 MN and p24 LAI titrations: goat anti-monkey IgG peroxydase conjugate (Cappel, ref. 55432) at 1/1,000
for the CPpp titrations: sheep anti-human Ig peroxydase conjugate (Amersham, ref. NA 933) at 1/300.

Antibody titers were calculated for the OD value range of 0.2 to 1.3, from the regression curve of a standard specific hyperimmune macaque serum present on each ELISA plate.

Neutralizing test were also carried out (FIG. 9). The assay determines the dilution of serum that prevents the development of syncytia in 50% of microwells infected with 10 CCID50 of HIV MN. The MN strain was obtained from F. Barré-Sinoussi and propagated in CEM clone 166 cells.

Sera were decomplemented and twofold serial dilutions in RPMI beginning 1/10 were prepared. Equal volumes of serum dilution and HIV suspension (500 μl each) were mixed and incubated for 2 hrs at 37° C. The HIV suspension had been adjusted to contain $10^2$ to $10^{2.5}$ CCID$_{50}$ per ml.

Prior to use, indicator CEMss cells were plated in microwells coated with poly-L-lysine, and incubated for 1 hr at 37° C. Culture medium was removed and replaced with the virus/serum mixtures (100 μl/well, 6 wells per dilution). After 1 hr incubation at 37° C., culture medium was added to each well and the plates were incubated at 37° C. All incubations were done in a 5% $CO_2$ incubator.

After 7 and 14 days respectively, the cultures were examined under the microscope and wells showing syncytia were recorded. Neutralizing 50% titer was computed according to SPEARMAN and KÄTER and expressed as the $log_{10}$ of the end-point. As a confirmation, supernatants of the cultures were collected on day seven, pooled for each dilution and assayed for reverse transcriptase (RT) activity.

Each assay included a set of uninfected microwells as negative controls, an infectivity titration of the virus suspension and a titration of antibody in a reference serunm.

3D—Serological Results

The mean antibody kinetics are presented in FIGS. 5 to 9.

gp160 MN/LAI Antibodies

All animals injected with gp160 MN/LAI only (group #1) seroconverted, although weakly, to the HIV protein after one immunization and consistently increased their response after the second and third inoculations (mean titers raised by +0.8 to +1.0 log two weeks post-injection). After the fourth immunization, titers reached similar levels than after the third one, and then decreased. The last inoculation induced a strong booster effect (mean titers raised by +1.3 log two weeks post-injection) and elicited the highest titers of the period examined (5.0 log on week 26).

A marked adjuvant effect of alum (group #2) was observed on the anti-gp160 antibody response in naive macaques. Indeed, as compared to the non-adjuvanted group (#1), the mean ELISA titers were enhanced by +1.0 to +2.0 log after each of the four first inoculations, and to a lesser extent after the fifth injection (+0.3 to +0.5 log). The highest levels of gp160-specific antibodies were obtained earlier than in group #1. This adjuvant effect was found to be significant (statistical analysis performed when possible, i.e. on weeks 4, 6 and 8, using the Dunnett's t-test).

Interestingly, the mixture (ALVAC-HIV+gp160) (group #3) was found to induce a significant higher response to gp160 than ALVAC-HIV after one or two inoculation(s) (group #4) (difference in mean titers up to +1.5 log). The anti-gp160 antibody titers were also more elevated in macaques injected with the mixture than in the vCP205-primed animals boosted with gp160 in alum (group #4). However, the differences were slight (+0.7 log maximum) and found to be significant only on weeks 20, 24 and 28 (group #4) (Newman-Keuls test).

The combination (ALVAC-HIV+gp160) also proved to be a better immunogen than gp160 alone (group #1) (mean titers between +0.8 to +1.7 log higher along the experiment), and did not strongly differ from gp160 adjuvanted in alum (group #2) (differences in mean titers=+/−0.5 log).

Finally, the prime/boost immunization regimen (group #4) induced in most cases higher antibody titers than inoculation with gp160 alone (group #1), especially after the gp160 boosts (differences up to +1.4 log), but lower responses than injection with gp160 in alum (group 42), particularly after the ALVAC priming (differences up to −2.0 log).

V3 MN Antibodies

On the whole, antibody responses elicited against V3MN shew a similar pattern than against gp160 MN/LAI, although to a lesser magnitude.

Alum (group #2) also increased the antibody titers to V3MN as compared to the non-adjuvanted group (#1), and this enhancing effect was found to be significant at weeks #2,4,6,8.

Animals injected with the mixture (ALVAC-HIV+gp160) (group #3) displayed significantly increased anti-V3MN responses than those receiving the prime/boost immunization (group #4) but only after the first and the second priming with ALVAC-HIV (weeks 4, 6 and 8) and following the last gp160 boost (weeks 26 and 28) (Newman-Keuls test). Moreover, similarly to what was seen on gp160, and although no statistical analysis could be performed given the low number of animals tested, the mixture raised V3MN responses higher than did gp160 alone (group #1) (titers augmented by +1.0 to +1.8 log), and close to those induced by gp160 adjuvanted in alum (group #2) (titers=+/−0.5 log in most cases).

p24 LAI Antibodies

In the group of macaques injected with the mixture (ALVAC-HIV+gp160) (#4), 2 animals out of 4 developed an antibody response against p24 LAI as compared to the preimmune samples: #11 became positive after two inoculations and titers increased by up to +1.3 log following the next immunizations; #18 clearly seroconverted after the third injection and maintained or decreased its response afterwards.

In group #5 receiving the prime/boost immunization, only 1 or possibly 2 from group #5 was (were) found to be positive on p24 LAI: #19 raised antibodies as soon as the first ALVAC priming; #22 was hardly positive after the last gp160 boost.

Anti-canarypox (CPpp) Antibodies

All macaques immunized against ALVAC-HIV vCP205 either two (group #4) or five (group #3) times elicited CPpp-specific antibodies two weeks after the first injection and reached their maximal responses after the second inoculation (week 6). Following the gp160 boosts in group #4, the anti-CPpp titers gradually decreased and were reduced by—1.0 log on week 28. In group #3, the mean antibody levels were maintained until week 14 (two weeks after the fourth injection), diminished (−0.7 log), and then increased to their maximum after the last booster immunization (week 26).

3E—HIV-1 MN Neutralizing Antibody Response

The mean titers of each group of macaques are presented in FIG. 9.

All the tested animals developed anti-HIV-1 MN neutralizing antibodies when examined after the fourth (week 16) and the fifth (week 26) injection, as compared to the preimmune samples (week 0).

Because of the low number of macaques studied in groups #1 and #2, no statistical comparison could be performed for these animals. However, the lowest neutralizing titers were observed in group #1 inoculated with non-adjuvanted gp160. In group #2 (except for week 26), injected with gp160 adjuvanted in alum, the neutralizing response was stronger than in group #1, similar on week 16 and higher on week 26 than in group #4 (prime/boost immunization), and slightly lower than in group #3 injected with the (ALVAC-HIV+gp160) mixture.

Paired comparisons of groups #3 and #4 by the Newman-Keuls test revealed no statistical difference on week 16 but showed that the mixture (ALVAC-HIV+gp160) (group #3) induced significantly higher neutralizing titers than the prime/boost immunization (group #4) on week 26.

General Conclusion

The present assay showed that the mixture vCP205 ($10^{6.5}$ $CCID_{50}$) plus gp160 (100 $\mu$g) elicited significantly higher gp160 and V3-specific responses than vCP205 or gp160 alone, and in some cases than the prime/boost immunization (vCP205/gp160 in alum), mainly after the final gp160 booster injection. The vCP205+gp16 mixture proved to be similarly immunogenic to gp160 adjuvanted in alum; given the low number of animals studied in the other groups. Moreover, the mixture appeared to evoke the best seroneutralizing responses to HIV-1-MN after the last fifth injection, although significance of this result could be proven only when compared with the prime/boost immunization, given the low number of animals in the other groups.

Example 4

Immunogenicity of Purified gp160 MN/LAI in the Absence or Presence of Canarypox (ALVAC), in Guinea-pigs The experiment reported in the present Example 4 shows that both crude and purified non-recombinant ALVAC (CPpp) display adjuvant properties.

4A—CPpp Preparations

CPpp (ALVAC) is derived from a canarypox strain isolated from a pox lesion on a infected canary, as described in Tartaglia et al, Virology (1992) 188:217. CPpp is produced on chick embryo fibroblasts in DMEM-Ham F12, washed without serum and resuspended in lactoglutamate (crude CPpp). Instead of being resuspended in lactoglutamate, purified CPpp is obtained according to the purification process described in Joklick et al, Virology (1962) 18:9.

4B—gp160 MN/LAI Preparation gp160 preparations were achieved as descibed in example 1B 4C—Experimental Procedure Guinea pigs were submitted to immunization protocols as described in Table 4 hereinafter.

TABLE 4

| Group (Guinea-pig #) | Primo-immunization (D1) | | | Booster (D29) |
|---|---|---|---|---|
| | gp160 dose (µg) | ALVAC (CPpp) | ALVAC dose (CCID50) | gp160 dose (µg) |
| 1 (1, 2, 3, 4, 5) | 5 | None | 0 | 5 |
| 2 (6, 7, 8, 9, 10) | 5 | Crude | $10^6$ | 5 |
| 3 (11, 12, 13, 14, 15) | 5 | | $10^6$ | 5 |
| 4 (16, 17, 18, 19, 20) | 5 | Purified | $10^7$ | 5 |
| 5 (21, 22, 23, 24, 25) | 5 | | $10^8$ | 5 |

Animals received both the primo and booster 1.10 ml doses intramuscularly (0.55 ml in each thigh) one month apart.

Serological analyses were carried out as described in Example 1C, using blood samples collected at days −1, 28 and 56.

4D—Serological Analyses

Serological analyses were carried out with blood samples collected on days −1. (one day before the first immunization), 28, and 56. Antibodies to HIV gp160 glycoprotein and CPpp were titrated by ELISA using the same procedure as described in example 1C 4E—Serological Results Anti-CPpp Antibodies (FIG. 10a)

Four weeks after the first immunization, all the animals seroconverted (except group #1 which did not received any CPpp), and the titers remained stable after the gp160 booster till week 8.

Response to canarypox induced by $10^6$ CCID$_{50}$ of crude CPpp was significantly higher (+0.7 to 0.8 logs) than the one raised with the same dose of purified virus, was comparable to that elicited by $10^7$ CCID$_{50}$ of purified CPpp, and was lower (~−0.8 log) than that obtained with the dose of $10^8$ CCID$_{50}$ of purified CPpp.

Anti-HIV gp160 MN/LAI Antibodies (FIG. 10b)

Anti-gp160 MN/LAI antibodies were elicited during the four weeks following the first injection in all animals, except some in group #5. In this group, which received a mixture of gp160 and $10^8$ CCID$_{50}$ of purified CPpp, only 3 animals out of 5 seroconverted to gp160. For each guinea pig, a booster effect was noticeable after the second injection of 5 µg of gp160.

The best anti-gp160 antibody responses were obtained in group #3, primed with gp160 mixed with the lowest dose ($10^6$ CCID$_{50}$) of purified CPpp. Indeed, this group displayed a significant increase in antibody titers (+0.8 and +0.9 logs at weeks 4 and 8, respectively), comparatively to group #1 inoculated with the protein alone.

Co-injection of $10^7$ CCID$_{50}$ of purified CPpp with gp160 (group #4) also enhanced the humoral response as compared to injection of the protein alone, but only on week 8 after the gp160 boost (+0.7 log). Surprisingly, in group #5 (gp160 mixed with $10^8$ CCID$_{50}$ of purified CPpp), a significant decrease in responding animals was observed (3 out of 5, versus 5 out of 5 in all other tested conditions). Moreover, the mean antibody titer (2.352 log) of the positive guinea pigs from group #5 was the lowest obtained in this assay.

Nevertheless, such a CPpp-induced inhibitory effect did not have any influence on the secondary response to gp160, which reached similar levels to those obtained in group #1.

Noticeably, addition of $10^6$ CCID$_{50}$ of crude CPpp to gp160 did not improve the antibody response as compared to gp160 alone.

General Conclusion

This study clearly demonstrates an adjuvant effect of crude and purified CPpp on the immunogenicity of gp160 MN/LAI inoculated IM in guinea pigs. Such a stimulation of the anti-gp160 antibody response was mostly observed at $10^6$ CCID$_{50}$ of purified CPpp, whereas a marked inhibitory effect was noted at the higher dose of $10^8$ CCID$_{50}$.

The results obtained with crude CPpp at $10^6$ CCID$_{50}$ indicates that this CPpp preparation does not seem to be able to enhance the anti-gp160 humoral response when combined with the 5 µg dose of the tested gp160. However, the same preparation does enhance the response to 1 µg gp160 (data not shown). Accordingly, the crude CPpp immunomodulating effect seems to be gp160-dose dependent.

Altogether, these findings show that both CPpp and gp160 must be used at optimal concentrations to see an adjuvant effect of canarypox. The present observation that both crude and purified CPpp can stimulate the anti-gp160 antibody response is in favor of the hypothesis that CPpp has intrinsic immuno-stimulating properties.

Example 5

Immunogenicity of gp160 MN/LAI in the Presence of Purified ALVAC-Luc (vCP292) Inactivated or not, in Guinea-pigs 5A—vCP297 Preparation vCP297 is an ALVAC vector derived from CPpp by homologous recombination so as to produce a vector in which the luciferase encoding sequence is placed under the control of an ALVAC promoter. vCP297 is produced and purified as described in Example 4A.

One ml of a vCP297 preparation exhibiting a mean titer of $10^{9.3}$ CCID$_{50}$ on QT35 cells, was diluted 1/10 in PBS without Cask and Mg$^{++}$ and inactivated at 56° C., 7 hours. It was then centrifuged during 5 hours at 10.000 rpm (centrifuge Sigman 201 M) and the pellet and supernatant were harvested separately. The protein quantity and residual viral titer were quantified, being respectively 55 µg/ml and $10^{3.5}$ CCID50/ml for the pellet and ≈1 µg/ml and $10^{0.3}$ CCID50/ml for the supernatant.

5B—gp160 Preparations Were Achieved as Described in Example 1B.

5C—Experimental Procedure

Guinea pigs were submitted to immunization protocols as described in Table 5 hereinafter.

TABLE 5

| Group (Guinea-pig #) | First immunization (D1) | | | Booster (D29) |
|---|---|---|---|---|
| | gp160 MN/LAI doses (µg) | Purified ALVAC-Luc (vCP297) | | gp160 MN/LAI doses (µg) |
| | | Proteins (µg) | Infectious dose (CCID50) | |
| 1 (1, 2, 3, 4, 5) | 5 | 0 | 0 | 5 |
| 2 (6, 7, 8, 9, 10) | | 0.055 | $10^5$ | |

TABLE 5-continued

| | First immunization (D1) | | | |
|---|---|---|---|---|
| | | Purified ALVAC-Luc (vCP297) | | Booster |
| Group (Guinea-pig #) | gp160 MN/LAI doses (μg) | Proteins (μg) | Infectious dose (CCID50) | (D29) gp160 MN/LAI doses (μg) |
| 3 (11, 12, 13, 14, 15) | | 0.55 | $10^6$ | |
| 4 (16, 17, 18, 19, 20) | | pelleted fraction of the inactivated virus 0.55 | $10^{1.5}$ | |
| 5 (21, 22, 23, 24, 25) | | supernatant of the inactivated virus after centrifugation¶ ~1 | $=10^{0.3}$ | |

Animals received the primo and booster doses under a final volume 1.10 ml, intramuscularly (0.55 ml in each thigh), one month apart.

Serological analyses were carried out as described in Example 1C, using blood samples collected at days −1, 28 and 56.

The isotypic distribution of the anti-gp160 humoral response was measured at day 56, using the procedure and conditions described in Examples 1C and 2C. The only modification was the use of distinct peroxydase-conjugated goat antibodies specific for guinea-pig isotype IgG1 (Nordic, ref.: GAGp/IgG1/PO) or IgG2 (Nordic, ref.: GAGp/IgG2/PO), diluted 1/3.000 in PBS-Tween-milk.

5D—Serological Results

Anti-CPpp Antibodies (FIG. 11a)

As previously observed, the humoral response induced against CPpp was dose-dependent: only 3 out of 5 guinea-pigs immunized with $10^5$ CCID$_{50}$ of purified ALVAC-Luc (vCP297) (group #2) weakly seroconverted to CPpp, whereas all animals (out of 5) that received $10^6$ CCID$_{50}$ of the purified virus (group #3) developed a CPpp-specific response, and at much higher levels (mean ELISA titer in group #3~2 logs higher than in group #2).

The anti-CPpp titers elicited by the pelleted fraction of the inactivated ALVAC-Luc (group #4) were similar to those induced by the non-inactivated virus at equivalent protein quantity (group #3).

Surprisingly, the supernatant of inactivation of vCP297 (group #5) was also able to mount an antibody response to the canarypox, and the titers induced were the highest observed in this assay. In particular, such a response differed in average by +0.6 and +0.9 log, on week 4 and 8 respectively, with that elicited by the non-inactivated purified virus (group #3). The high protein content present in this supernatant—measured subsequently to inoculation—reaching ~1 μg versus 0.55 μg for both the non-inactivated virus (group #3) or the pelleted fraction of the inactivated virus (group #4) could account for such results.

Anti-gp160MN/LAI Antibodies (FIG. 11b)

Anti-gp160MN/LAI antibodies were elicited in all animals during the four weeks following the first injection. For each guinea pig, an anarnnestic response was noticeable after the gp160 booster injection.

While no significant difference in anti-gp160 antibody titers was detected between the five groups of guinea pigs after the primo-immunization, an enhancement of the humoral response to the HIV antigen was observed in some groups after the second inoculation. Indeed, by variance analysis using the Dunnett's t-test, the gp160-specific ELISA titers were found to be significantly higher in groups #3 and #4 than in group #1 (mean titers on week 8 in both groups #3 and 4 raised by +0.7 log as compared to group #1). In other words, these findings indicated that purified ALVAC-Luc, either inactivated or not, at protein quantity corresponding to $10^6$ CCID$_{50}$ of infectious virus, had a significant adjuvant effect on the anti-gp160 antibody secondary response.

Priming with gp160 and purified ALVAC-Luc at $10^5$ CCID$_{50}$ (group #2) also increased the anti-gp160 response (mean titers on week 8 raised by +0.4 log as compared to group #1), but such a stimulation was not found to be significant using the Dunnett's t-test.

By contrast, a significant adjuvant effect was detected in group #5, co-injected with gp160MN/LAI and the supernatant of inactivated purified ALVAC-Luc, (mean titers on week 8 raised by +0.5 log as compared to group #1), in accordance with the high protein content of ALVAC-Luc origin found in the supernatant.

Noticeably, the stimulating effect on the anti-gp160 humoral response associated to ALVAC-Luc, or products derived from it, was not found to be strictly related to the intensity of the anti-CPpp antibody response elicited. This confirms previous observations in Example 1, showing that high anti-CPpp titers were inversely related to anti-gp160 antibody levels, probably as a consequence of antigenic competition between the HIV glycoprotein and the high doses of ALVAC injected.

IgG1 and IgG2 Isotypic Profiles of the Anti-gp160 Antibody Response

The co-injection of gp160 and ALVAC-Luc, either inactivated or not (at protein quantity corresponding to $10^6$ CCID$_{50}$ of infectious virus), was found to significantly increase the anti-gp160 antibody response of the IgG2 isotype, but not of the IgG1 one. Such an elevated IgG2 response was detected neither in group #2, that received gp160MN/LAI and $10^5$ CCID$_{50}$ of purified recombinant canarypox, nor in group #5, injected with gp160MN/LAI and the supernatant of inactivated ALVAC-Luc.

General Conclusion

The data presented herein confirm those obtained in Example 1 with purified CPpp, showing that purified recombinant canarypox ALVAC-Luc (vCP297), when co-injected with gp160MN/LAI at the dose of $10^6$ CCID$_{50}$ in guinea-pig, had also the capacity to significantly: (1) stimulate the gp160-specific IgG secondary response; and (2) influence the isotypic profile of the anti-gp160 antibodies (increase in specific IgG2 titers). However, this adjuvant effect was detected earlier with CPpp than with vCP297 (i.e., after the primo-immunization for the former versus only the gp160 boost for the latter), suggesting that recombinant ALVAC-Luc might be less effective in enhancing the humoral response than the parental vector.

Infectivity of ALVAC-Luc was not required for such a stimulating effect to occur, since both the non-inactivated and heat-inactivated recombinant canarypox, at equivalent protein quantity (corresponding to that contained in $10^6$ CCID$_{50}$ of infectious virus), induced similar enhanced anti-gp160 antibody titers.

The observation that the supernatant of inactivated purified ALVAC-Luc also displayed an adjuvant effect on the anti-gp160 antibody response was unexpected, but could be explained by its high protein content of ALVAC-Luc origin. Its ability to elicit the highest antibody titers against CPpp but not against gp160, confirms the results obtained in Example 1 using various doses of purified ALVAC.

Altogether, these findings are in line with the previous hypothesis that the canarypoxvirus induces some immunomodulating effects in vivo.

Example 6

Immunogenicity and Efficacy of a Detergent-splitted Monovalent A/Texas Flu Vaccine in the Absence or Presence of Canarypox (ALVAC) in Mice The experiment reported in the present example 6 shows that non-recombinant ALVAC increases the immunogenicity and the efficacy of a detergent-splitted flu vaccine essentially in aged immunocompromised mice.

6A—CPpp Preparation

CPpp preparations were achieved as described in Example 4A. The titer of the stock CPpp preparation is 1.6 $10^9$CCID 50/ml.

6B—Detergent-splitted Monovalent A/Texas Flu Vaccine Preparation

The detergent-splitted monovalent A/Texas flu vaccine (A/Texas) was manufactured by Connaught laboratories and dialyzed against PBS before use, to eliminate residual detergent and formol from the vaccine.

6C—Serological Analyses

Serological analyses were cared out with blood samples collected on days −4 (4 days before the first immunization), 14 and 35. Antibodies to HA were titrated as follows: Wells of Maxisorp F96 NUNC plates were coated with 1 $\mu$g/ml of HA in a Carbonate buffer 0.1 M, pH 9.6 overnight at room temperature. Plates were then blocked for 1 hour at room temperature With 200 $\mu$l of 0.1% BSA (Bovine Serum Albumin) in PBS Followed by 4 washings in washing buffer (PBS/0.1% Tween 20). All next incubations were carried out in a final volume of 100 $\mu$l, followed by 5 washings in washing buffer.

Serial threefold dilutions of sera in dilution buffer (PBS/0.1% Tween 20/0.1% BSA) ranging from 1/100 to 1/218700 were added to the wells and incubated 60 min at 37° C. After washings, a Sheep anti-mouse IgG1 peroxydase conjugated (Serotec) 1/15000 diluted or a Goat anti-mouse IgG2a Horseradish peroxydase conjugated (Caltag laboratories)1/30000 diluted were added to the plates and incubated for another 60 min at 37° C. The plates were farther washed and incubated for 20 min with O-phenylenediamine dihydrochloride (Sigma) at 1.5 mg/ml in 0.05 M phosphate citrate buffer, pH 5.0 containing 0.03% sodium perborate (Sigma). The colored reactions were stopped with 50 $\mu$l of 4N $H_2SO_4$. Absorbance was read in a Titer Multiscan plate reader at 450 nm. The antibody titers were measured as the reciprocal of the last dilution at which the absorbance was 2 fold over the background absorbance obtained with pre-immune sera.

6D—Challenge

Randomized groups of mice were challenged on day 42 with 50 $\mu$l of live mouse-adapted A/Taiwan/1/86 influenza virus (H1 strain) corresponding to 5 lethal doses 50 of virus (5 $LD_{50}$). The infectious doses were given intranasally after slight anesthesia of mice with Isoflurane. The protective immune responses induced by the tested vaccinal compositions were assessed by means of survival yields and weight changes that is a good parameter of morbidity. Mortality and weight changes in the mice were monitored daily and every pair day respectively up to 21 days after challenge. The article Suryaprakash S and al, (1997), 96:157–169 is cited by reference for achieving experimental challenges.

6E—Immunization

Six randomized groups of 16-to-18 month old (aged) or 2-month old (young) DBA/2 mice were each submitted to one of the immunization protocol as described in Table 6 hereinafter. Each group is constituted with 6 mice.

TABLE 6

| Group DBA/2 | Primo-immunization | | Boost | |
| --- | --- | --- | --- | --- |
| | A/Texas dose (in $\mu$g) | ALVAC (CPpp) dose (in CCID 50) | A/Texas dose (in $\mu$g) | ALVAC (CPpp) dose (in CCID 50) |
| 1 | 3 | 0 | 3 | 0 |
| 2 | 3 | $2 \times 10^7$ | 3 | $2 \times 10^7$ |
| 3 | 0 | $2 \times 10^7$ | 0 | $2 \times 10^7$ |

The groups were primed and boosted, via the S.C. route, with the compositions in a final volume of 0.2 ml. For immunization of group 2, A/Texas and appropriate amount of ALVAC were mixed together with appropriate amount of PBS to bring the final injected volume to 0.2 ml per mouse. The booster immunization was carried out in all groups one month later.

6F—Serological Results

Anti A/Texas IgG1 Antibodies (FIG. 12)

Anti-A/Texas IgG1 antibodies were elicited during the two weeks following the first injection in 3 to 6 mice from group 1, in 5 to 6 mice from group 2, whereas no specific IgG1 were elicited in mice primed with ALVAC alone (group 3). The specific IgG1 mean titer was approximately 10 fold higher in the group of mice primed with the mixture of A/Texas and CPpp (group 1) than that observed in the group of mice given A/Texas alone (group 2). The boost did not change the distribution pattern of specific IgG1 responses (observed in the 3 groups of mice) during the 15 days following the second injection. However, the specific IgG1 mean titers of groups 1 and 2 were ten-fold higher.

Anti A/Texas IgG2a Antibodies (FIG. 13)

Anti-A/Texas IgG2a antibodies were elicited during the two weeks following-the first injection in 3 to 6 mice from group 1, in 5 to 6 mice from group 2, whereas no specific IgG2a were elicited in mice primed with ALVAC alone (group 3). The specific IgG2a mean titer was approximately 10 fold higher in the group of mice primed with the mixture of A/Texas and CPpp (group 1) than that observed in the group of mice given A/Texas alone (group 2). The boost did not change the distribution pattern of specific IgG2a responses (observed in the 3 groups of mice) during the 15 days following the second injection. However, the specific IgG2a mean titers of groups 1 and 2 were ten-fold higher.

General Conclusion

This study clearly demonstrates an adjuvant effect of CPpp on the immunogenicity of A/Texas inoculated subcutaneously in immunocompromised aged mice. A similar enhancer supportive effect of CPpp on the immunogenicity of A/Texas is also observed in young mice. It is also worth noticing that CPpp increases both specific IgG2a and IgG1 responses in old mice immunized with the mixture of ALVAC and A/Texas; which means that CPpp could act both on TH1 (T helper 1) and TH2 (T helper 2) immune responses. Indeed, it is well understood for a man skilled in the art that the, TH2 immune response correlates with the level of specific IgG1 response in mice and is featured by a rather humoral immune response, whereas the TH1 immune response correlates with the level of specific IgG2a response and is commonly featured by a cytotoxic and inflammatory immune response. In conclusion, this reveals that CPpp acts both on specific cellular and humoral immune responses, when it is concomitantly administered with an immunogenic compound.

6G—Challenge Results (FIGS. 14 and 15)

Mortality (FIG. 14)

Three weeks after the boost, all the aged mice were given intranasally a lethal challenge of live influenza virus. All the 6 mice of the group 3 (group receiving CPpp alone) died during the 8 days consecutive to challenge. Only, 1 of 6 mice (16% survival rate) of the group 1 (group receiving A/Texas alone) was still alive 20 days after challenge whereas 4 of 6 mice of the group 2(group receiving the mixture A/Texas and CPpp) (66% survival rate) were still alive. Moreover, the survival curve of group 2 clearly shows that the two deaths observed were delayed compared to those observed in groups 1 and 3 (FIG. 14)

Morbidity (FIG. 15)

The morbidity of mice after challenge was monitored for 20 days and assessed by the weight loss rate. The weight loss occurred shortly after the challenge in the group of mice immunized with CPpp alone (group 3) reaching up to 35% of the initial weight. Mice immunized with A/Texas alone (group 1) also showed a severe weight loss after challenge similar to that observed in group 3. The weight loss rate curve during the 20 days of the monitoring for the only one survivor of group 1 is represented in FIG. 15 and clearly shows that the weight loss was fast and severe, whereas the weight recovery was much slower. On the other hand, the weight loss rate curve involving the 4 survivors of group immunized with the mixture of ALVAC and A/Texas (group 2) shows improvements over group 1. First, the maximum weight loss rate did not exceed 15% of the initial weight and second, the weight recovery was faster, since the survivors had recovered their initial weight by the end of the monitoring.

Although morbidity and mortality results about aged mice only are reported here, it is indicated that similar results were obtained with young mice.

General Conclusion

Morbidity and mortality results obtained with the live influenza challenge model are in agreement with those obtained from immunogenicity studies and show that ALVAC is not only able to enhance the specific immune response to A/Texas but also contributes to the elicitation of a specific protective immune response, when it is co-administered with an antigen from a pathogenic microorganism.

What is claimed is:

1. A composition comprising (i) an immunogenic compound and (ii) a poxvirus encoding an heterologous polypeptide which is selected from the group consisting of adhesion molecules, co-immunostimulatory molecules, chemokines apoptotic factors, cytokines and growth hormones.

2. The composition according to claim 1, wherein the immunogenic compound is selected from the group consisting of a peptide, a polypeptide, a DNA plasmid encoding a peptide or a polypeptide, and an hapten coupled to a carrier molecule.

3. A composition comprising (i) an immunogenic compound which is a first polypeptide, and (ii) a poxvirus encoding a second heterologous polypeptide, which has an amino acid sequence identical to the amino acid sequence of the first polypeptide.

4. A composition comprising (i) an immunogenic compound which is a DNA plasmid encoding a first polypeptide, and (ii) a poxvirus encoding a second heterologous polypeptide, which has an amino acid sequence identical to the amino acid sequence of the first polypeptide.

5. The composition according to claim 2, wherein the first and second polypeptide are HIV or influenza virus polypeptides.

6. A method of enhancing a specific immune response to an immunogenic compound in a vertebrate, the method comprising administering to the vertebrate a composition comprising a poxvirus and the immunogenic compound.

7. The method according to claim 6, wherein the immunogenic compound comprises at least one antigenic determinant of a pathogenic microorganism or a tumor-associated antigen.

8. The method according to claim 7, wherein a protective immune response against the pathogenic microorganism or tumor is induced.

9. The method according to claim 8, wherein said administering treats or prevents an infectious disease induced by the pathogenic microorganism or a disorder associated with the tumor.

10. The method according to claim 6, wherein the immunogenic compound is a peptide or a polypeptide.

11. The method according to claim 10, wherein the peptide or polypeptide is from a pathogenic microorganism or is tumor associated antigen.

12. The method according to claim 10, wherein the peptide or polypeptide is from HIV or an influenza virus.

13. The method according to claim 6, wherein the immunogenic compound is a recombinant DNA plasmid encoding a peptide or a polypeptide that comprises at least one antigenic determinant of a pathogenic microorganism or tumor-associate antigen.

14. The method according to claim 13, wherein the administering induces a protective immune response against the pathogenic microorganism or tumor.

15. The method according to claim 14, wherein said administering treats or prevents an infectious disease induced by the pathogenic microorganism or a disorder associated with the tumor.

16. The method according to claim 13, wherein the peptide or polypeptide is from HIV or influenza virus.

17. The method according to claim 6, wherein the immunogenic compound is an hapten coupled to a carrier molecule.

18. The method according to claim 6, wherein the poxvirus is a live virus.

19. The method according to claim 18, wherein the poxvirus is attenuated.

20. The method according to claim 6, wherein the poxvirus is an inactivated virus.

21. The method according to claim 6, wherein the poxvirus does not encode a heterologous polypeptide.

22. The method according to claim 6, wherein the poxvirus encodes a heterologous polypeptide.

23. The method according to claim 22, wherein the heterologous polypeptide is selected from the group consisting of adhesion molecules, co-immunostimulatory molecules, apoptotic factors, cytokines and growth hormones.

24. The method according to claim 22, wherein the heterologous polypeptide is different from and immunologically cross-reactive with the immunogenic compound.

25. The method according to claim 22, wherein the heterologous polypeptide has an amino acid sequence identical to the immunogenic compound.

26. The method according to claim 6, wherein the poxvirus is selected from the group consisting of orthopoxvirus, avipoxvirus, capriposvirus, suipoxvirus, molluscipoxvirus, yataposvirus, or an entomopoxvirus.

27. The method according to claim 6 wherein the poxvirus is a vaccinia virus.

28. The method according to claim 6 wherein the poxvirus is a canarypoxvirus.

* * * * *